(12) United States Patent
Evans et al.

(10) Patent No.: US 9,581,587 B2
(45) Date of Patent: Feb. 28, 2017

(54) SPERM STAINING AND SORTING METHODS

(71) Applicant: INGURAN, LLC, Navasota, TX (US)

(72) Inventors: Kenneth Michael Evans, College Station, TX (US); Thomas B. Gilligan, College Station, TX (US); Clara Gonzalez-Marin, College Station, TX (US)

(73) Assignee: Inguran, LLC, Navasota, TX (US)

( * ) Notice: Subject to any disclaimer, the term of this patent is extended or adjusted under 35 U.S.C. 154(b) by 41 days.

(21) Appl. No.: 14/348,194

(22) PCT Filed: Sep. 28, 2012

(86) PCT No.: PCT/US2012/058008
§ 371 (c)(1),
(2) Date: Mar. 28, 2014

(87) PCT Pub. No.: WO2013/049631
PCT Pub. Date: Apr. 4, 2013

(65) Prior Publication Data
US 2014/0234833 A1 Aug. 21, 2014
US 2015/0072340 A2 Mar. 12, 2015

Related U.S. Application Data

(60) Provisional application No. 61/541,438, filed on Sep. 30, 2011, provisional application No. 61/541,451, filed on Sep. 30, 2011.

(51) Int. Cl.
*G01N 33/50* (2006.01)
*G01N 21/64* (2006.01)
*C12N 5/076* (2010.01)

(52) U.S. Cl.
CPC ......... *G01N 33/5005* (2013.01); *C12N 5/061* (2013.01); *G01N 21/6428* (2013.01); *G01N 2021/6432* (2013.01); *G01N 2021/6441* (2013.01)

(58) Field of Classification Search
None
See application file for complete search history.

(56) References Cited

U.S. PATENT DOCUMENTS

| | | | |
|---|---|---|---|
| 4,559,309 A | 12/1985 | Evenson et al. | |
| 5,135,759 A | 8/1992 | Johnson et al. | |
| 5,895,922 A | 4/1999 | Ho | |
| 6,149,867 A | 11/2000 | Seidel et al. | |
| 7,070,917 B1 * | 7/2006 | Christensen | G01N 15/1012 435/2 |
| 7,208,265 B1 * | 4/2007 | Schenk | 435/1.1 |
| 7,582,432 B2 | 9/2009 | Cook et al. | |
| 9,140,688 B2 | 9/2015 | Evans et al. | |
| 2005/0003472 A1 | 1/2005 | Anzar et al. | |
| 2006/0040400 A1 | 2/2006 | Mizutani et al. | |
| 2006/0067916 A1 | 3/2006 | Schenk et al. | |
| 2009/0176271 A1 | 7/2009 | Durack et al. | |
| 2009/0208977 A1 | 8/2009 | Hudson et al. | |
| 2013/0011825 A1 | 1/2013 | Moreno et al. | |
| 2013/0084558 A1 | 4/2013 | Evans et al. | |
| 2014/0099627 A1 | 4/2014 | Gilligan et al. | |
| 2014/0099628 A1 | 4/2014 | Evans et al. | |

FOREIGN PATENT DOCUMENTS

| | | |
|---|---|---|
| WO | 0137655 A1 | 5/2001 |
| WO | 02/41906 A2 | 5/2002 |
| WO | 2005095960 A1 | 10/2005 |
| WO | 2009/014456 A1 | 1/2009 |
| WO | 2010/150013 A2 | 12/2010 |
| WO | 2011/053727 A2 | 5/2011 |
| WO | 2011/123166 A2 | 10/2011 |
| WO | 2013/049631 | 4/2013 |

OTHER PUBLICATIONS

ThermoFisher, Hoechst 33342 Solution, retrieved from the internet, Oct. 29, 2015: www.thermofisher.com/order/catalog/product/62249.*
FD&C Red Dye 40 Information, Education and Discussion, Red 40, retrieved from the internet Oct. 29, 2015: www.red40.com/.*
Dartmouth et al., ChemLab, Color and Light, retrieved from the Internet Apr. 21, 2016: www.dartmouth.edu/~chemlab/chem6/dyes/full_text/chemistry.html.*
Natural Sourcing, MSDS, FD & C Red 40 Dye Powder, retrieved from the Internet Apr. 21, 2016: www.naturalsourcing.com/msds/MSDS_FDC_Red_40_Powder.pdf.*
Setareh Biotech, product details: Ethidium Homodimer-2 www.setarehbiotech.com/details.cfm?ProdID=553.*
Strober, Warren. "Trypan blue exclusion test of cell viability", Current protocols in immunology (2001): A-3B. (2 pp).
"Characteristics of Deionised Water", 2004 (6 pp).
US FDA Brochure, "Food Color Facts", 1993 (5 pp).
U.S. Office Action dated Dec. 19, 2014, issued in related U.S. Appl. No. 13/631,249.
Johnson et al., "Improved Flow Sorting Resolution of X- & Y-Chromosome Bearing Viable Sperm Separation Using Dual Staining and Dead Cell Gating." Cytometry, vol. 17, Supplement 7, Abstract, p. 83 (1994).
Garner, D.L., "Hoechst 33342: The dye that enabled differentiation of living X-and Y-chromosome bearing mammalian sperm", Theriogenology 71 (2009) 11-21.

(Continued)

*Primary Examiner* — Thane Underdahl
*Assistant Examiner* — Yvonne Pyla
(74) *Attorney, Agent, or Firm* — Ryan Christensen; Hashim Rahman

(57) ABSTRACT

A method of sex sorting sperm is disclosed. The sperm may be stained with a DNA selective fluorescent dye, which fluoresces when excited, a dead quenching dye, which selectively quenches fluorescence emitted by the DNA selective fluorescent dye within the membrane of compromised sperm, and a split enhancing dye. The stained sperm may then sorted into one or more gender enriched subpopulations of viable sperm.

14 Claims, 10 Drawing Sheets

(56) References Cited

OTHER PUBLICATIONS

Stap et al., "Improving the Resolution of Cryopreserved X- and Y-Sperm During DNA Flow Cytometric Analysis with the Addition of Percoll to Quench the Fluorescence of Dead Sperm" J. Anim. Sci., 1998, 76, 1896-1902.

Klinc, "Improved Fertility of Flowcytometrically Sex Selected Bull Spermatozoa" Inaugural-Dissertation, 2005, 1-108.

Johnson, Lawrence A., and Welch, Glenn R., "Evaluation of Bisbenzimidazole Analogs for Use in Flow Cytometric DNA Analysis of X- and Y-Bearing Sperm." U.S. Dept. of Agriculture, ARS, Reproduction Lab, Beltsville, MD USA, 1991, p. 86.

McNutt, Tamara L. and Johnson, Lawrence A., "Flow Cytometric Sorting of Sperm: Influence on Fertilization and Embryo/Fetal Development in the Rabbit," Molecular Reproduction and Development, 43, 1996, pp. 261-267.

Montano, G.A., Kraemer, D.C., Robeck, T.R., and O'Brien, J.K., "Evaluation of motility, membrane status and DNA interity of frozen-tawed bottlenose dolphin (*Tursiops truncatus*) spermatozoa after sex-sorting and recryopreservation," Societ for Reproduction and Fertility, Mar. 27, 2012, pp. 1-50.

Rath D et al., "Improved quality of sex-sorted sperm: A prerequisite for wider commercial application," Theriongenology, Jan. 1, 2009, vol. 71, No. 1, Los Altos, CA, US, pp. 22-29.

Seidel, George E., "Sexing Mammalian Sperm—Where Do We Go from here?" Journal of Reproduction and Development, vol. 58, No. 5, 2012, pp. 505-509.

Seidel et al., "Current status of sexing mammalian spermatozoa" Reproduction, 2002, 124, pp. 733-743.

International Search Report issued in corresponding PCT Application No. PCT/US2011/058008 dated Nov. 29, 2012.

Cytomation product information, retrieved from the Internet: www.cyto.purdue.edu/cdroms/cyto5/sponsors/cytomate/moflo.htm; retrieved on-line May 13, 2014, (3pp).

U.S. Office Action dated Jun. 3, 2014, issued in related U.S. Appl. No. 13/631,249 (32 pp).

EP Examination Reported dated Jul. 7, 2015 issued in related EP application No. 12775394.5.

US Notice of Allowance dated Jul. 15, 2015 issued in related U.S. Appl. No. 13/631,249.

\* cited by examiner

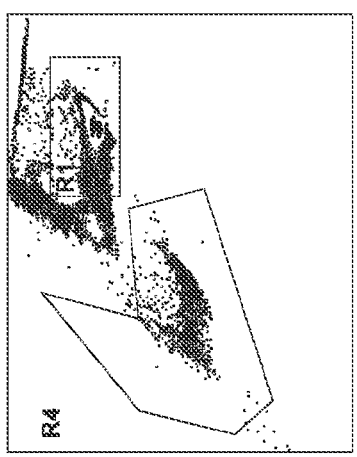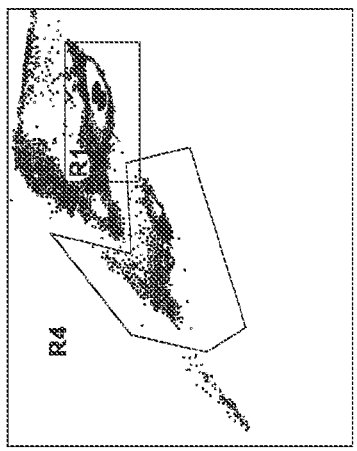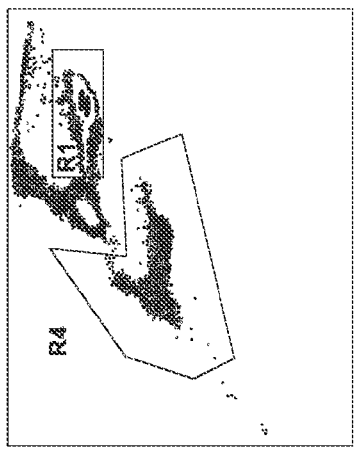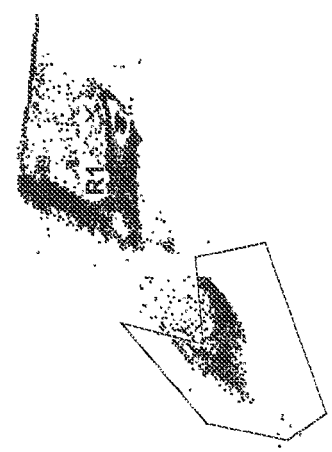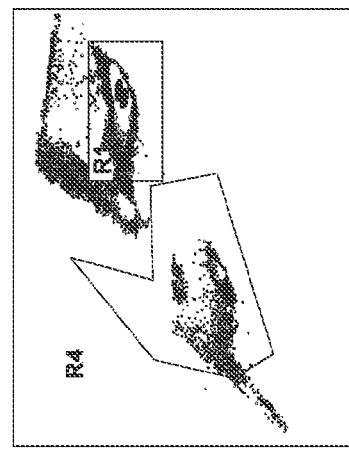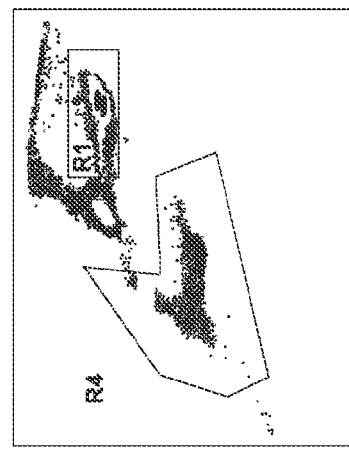
FIG. 3

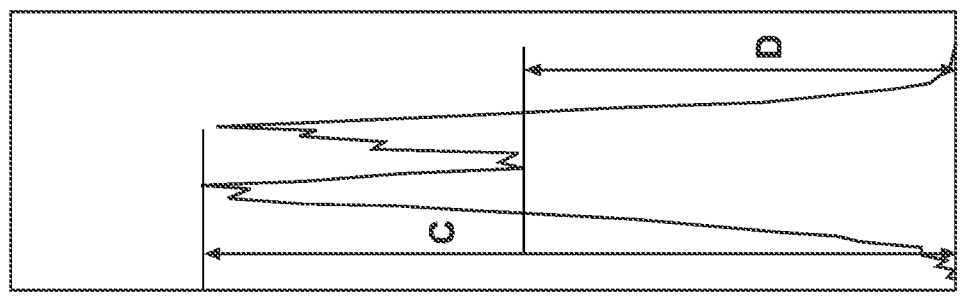
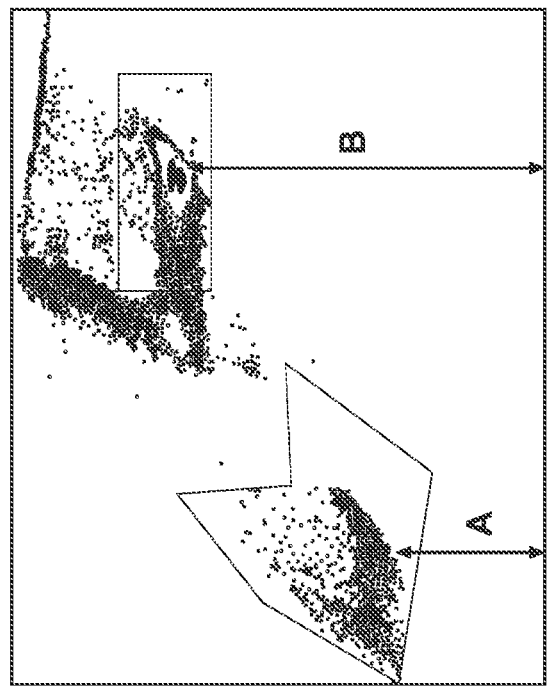
FIG. 4

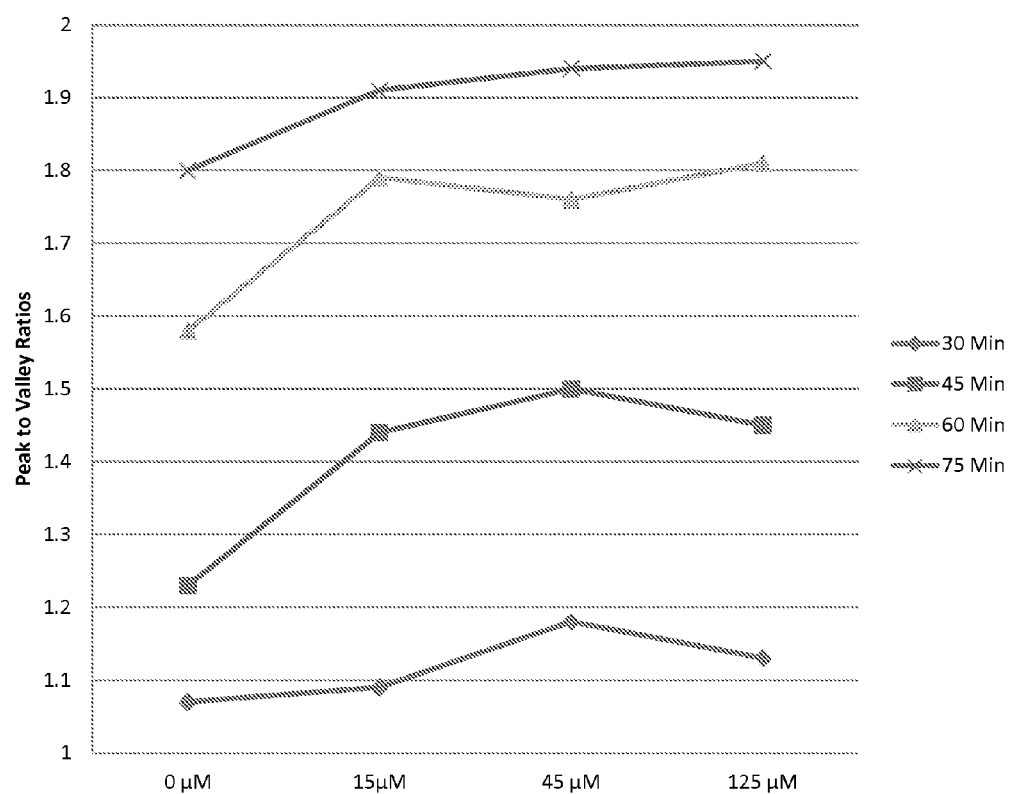

SPERM STAINING AND SORTING METHODS

This application is a National Stage of International Application No. PCT/US2012/058008, filed Sep. 28, 2012, which claims the benefit of U.S. Provisional Application No. 61/541,438, filed on Sep. 30, 2011, and U.S. Provisional Application No. 61/541,451, filed on Sep. 30, 2011, each are hereby incorporated herein by reference.

TECHNICAL FIELD

Generally, this disclosure relates to staining and sorting methods, such as Fluorescence Activated Cell Sorting (FACS), and more particularly this disclosure relates to staining and sorting methods which improve sort parameters in flow cytometry.

BACKGROUND

Effective pre-selection of sex has been accomplished in many species following the development of reliable methods for separating sperm into enriched X-chromosome and/or Y-chromosome bearing subpopulations. Traditional sperm sorting methods often rely on FACS for the detection of quantifiable differences in DNA content of X-chromosome bearing sperm and Y-chromosome bearing sperm, such as through flow cytometry. A typical step in these methods includes staining a sperm population with a DNA selective fluorescent dye that uniformly stains nuclear DNA. Hoechst 33342, sometimes referred to as Hoechst bisbenzimide 33342, is the most widely utilized stain for this purpose because it can be used in a sufficient quantity to differentiate small variations in nuclear DNA without exhibiting the toxicity of other fluorescent stains.

Sorted sperm quality and purities improved with the introduction of a dead quenching dye for differentiating membrane compromised sperm from the population or populations of interest. Membrane compromised sperm can include dead and dying sperm, which may have fragmented and disintegrating nuclear DNA that obscures the already narrow differences in X-chromosome bearing sperm and Y-chromosome bearing sperm. Initially, propidium iodine was used for this purpose, but has been shown to be toxic to sperm. Later, FD&C red food dye No. 40, 6-hydroxy-5-[(2-methoxy-5-methyl-4-sulfophenyl)azo]-2-naphthalenesulfonic acid (hereafter "red food dye No. 40" or "red 40"), was added to the sperm staining process as the dead quenching dye for quenching membrane compromised sperm and removing membrane compromised sperm from the sort analysis.

When sex sorting sperm, ultimately a small variation in DNA content is quantified differentiating X-chromosome bearing sperm from Y-chromosome bearing sperm. In bovine, for example, Holsteins have about a 3.8% difference in DNA content, while Jersey bulls have about a 4.1% difference. Due to the inexact nature of stoichiometric DNA staining, these small differences can be difficult to differentiate. This difficulty may be exacerbated by noise in the DNA staining complex, which can vary randomly in both X-chromosome bearing sperm and Y-chromosome bearing sperm.

One previously unrealized problem that may exist in current dead quenching staining regiments may be an over quenching of some desired signal. This may occur with the presence of a dead quenching dye in a sperm sample which does not associate with membrane compromised sperm, but instead remains in the sample quenching signals produced by membrane compromised sperm and non-membrane compromised sperm alike. It may also be that some dead quenching dye associates with healthy sperm cells. For these reasons, quenching in the sample may slightly quench the overall signal. While this may be happening to a far extent as compared to the quenching of membrane compromised sperm, it can be relevant when attempting to differentiate small differences in nuclear DNA content.

The sperm sorting process is damaging to cells which are non-regenerative time critical cells. The staining step can be the especially harmful. While Hoechst 33342 can be used in non-toxic concentrations, sperm must be incubated at elevated temperatures and elevated pHs for sufficient Hoechst 33342 penetration with sufficient uniformity for analysis or sorting. Each of elevating sperm temperature and elevating sperm pH may contribute to sperm damage. Therefore, a need exists for improvements to the staining process which reduce stain times or reduce incubation temperatures and/or pHs. Additionally, many chemicals added during sperm processing negatively impact sperm viability. This can be particularly true in sperm staining and sorting procedures.

DISCLOSURE OF INVENTION

Certain embodiments of the claimed invention are summarized below. These embodiments are not intended to limit the scope of the claimed invention, but rather serve as brief descriptions of possible forms of the invention. The invention may encompass a variety of forms which differ from these summaries.

One embodiment relates to a method of gender enriching one or more sperm subpopulation utilizing a dead quenching dye and a split enhancing dye. Such a method can begin by obtaining a population of sperm which includes both X-chromosome bearing sperm and Y-chromosome bearing sperm. At least a portion of that sperm can be stained with a DNA selective fluorescent dye which fluoresces when excited. The stained portion of sperm may then be further stained with a dead quenching dye which selectively quenches fluorescence emitted by the DNA selective fluorescent dye within the membrane of compromised sperm. The stained portion of sperm may additionally be stained with a split enhancing dye and then sorted into one or more gender enriched subpopulations of viable sperm.

Another embodiment relates to a method for gender enriching one or more sperm subpopulations with a dead quenching dye having a yellow or orangish color. Such a method can begin by obtaining a population of sperm which includes both X-chromosome bearing sperm and Y-chromosome bearing sperm. At least a portion of that sperm can be stained with a DNA selective fluorescent dye which fluoresces when excited. The stained portion of sperm may then be further stained with a dead quenching dye which selectively quenches fluorescence emitted by the DNA selective fluorescent dye within the membrane of compromised sperm. The dead quenching dye may be yellow, orange, or orangish red in appearance. Finally, the stained sperm may be sorted into one or more gender enriched subpopulations of viable sperm.

Still another embodiment relates to a sex sorted sperm suspension in the form of either an intermediate product in the sorting process, or as an artificial inseminate. The sex sorted sperm suspension can include viable, sex sorted sperm including an associated DNA selective fluorescent dye. The suspension may additionally include a medium supporting sperm viability, as well as, a second dye and a third dye.

BRIEF DESCRIPTION OF DRAWINGS

FIG. 3 illustrates bivariate histograms from a flow cytometer sorting sperm with different dead quenching dyes.

FIG. 4 illustrates an example of parameters measured from a univariate and bivariate plot in a flow cytometer.

FIG. 9 illustrates a graphical representation of a split enhancing capacity at various concentrations.

Figure 1:
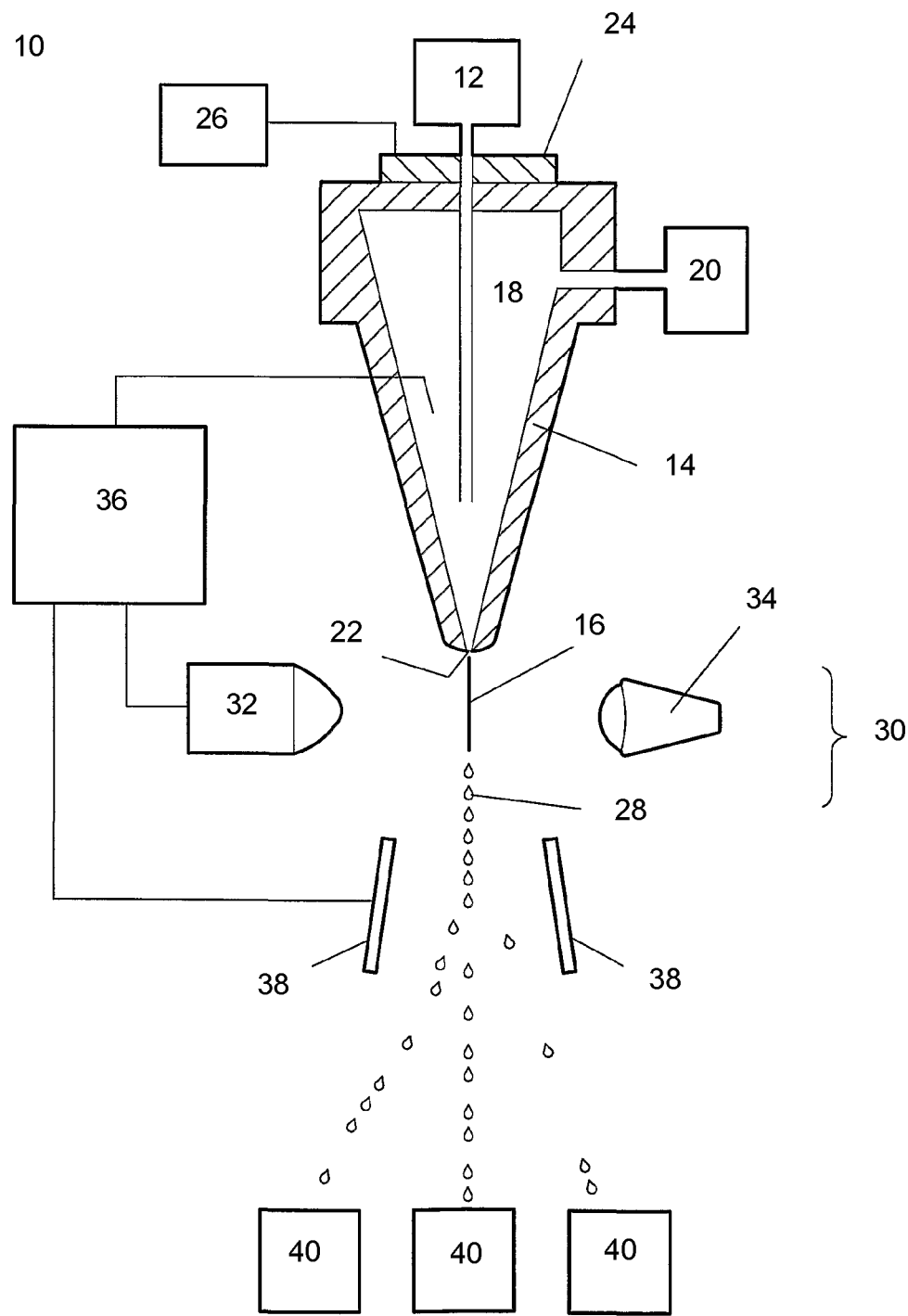
FIG. 1 illustrates a representation of a jet-in-air flow cytometer used in certain embodiments described herein.

While the present invention may be embodied with various modifications and alternative forms, specific embodiments are illustrated in the figures and described herein by way of illustrative examples. It should be understood the figures and detailed descriptions are not intended to limit the scope of the invention to the particular form disclosed, but that all modifications, alternatives, and equivalents falling within the spirit and scope of the claims are intended to be covered.

MODES FOR CARRYING OUT THE INVENTION

In certain aspects the present invention provides improved staining procedures with particular benefits in the sex selection or sex sorting of sperm. For example, certain aspects relate to improvements in sorting sperm by quenching undesirable noise arising from random signal variations produced by undesired dead cells and reducing undesirable non-specific noise arising from viable cells. Another aspect relates to an improved dead quenching dye which with an improved capacity to quench signals from dead sperm. These aspects may provide independent benefits in sort speeds or improved sort purities, or may be combined to synergistically further improve sorting. Alternatively, stain concentrations or stain times and other harmful aspects of staining may be reduced with the described improvements while maintaining acceptable sorting parameters, such as speed and purity, perhaps resulting in improved motility and viability in the sorted sperm sample.

Existing staining protocols for sex sorting, or even bulk sorting, sperm rely up the inclusion of F&DC red food dye No. 40 ("red food dye No. 40" or "red 40") as a dead quenching dye. The maximal absorbance wavelengths of red food dye No. 40 overlaps the maximal emissions wavelengths of fluorescent dyes, including Hoechst 33342 when bound to nuclear or chromosomal DNA. Because red food dye No. 40 differentially permeates membrane compromised sperm cells and overlaps the emission spectra of the DNA selective fluorescent dye, FRET (florescence resonance energy transfer) between the light leaving the DNA-stain complex and the dead quenching dye reduces the overall detected intensity of the light emitted from membrane compromised sperm. The quenched, or dampened, fluorescence from these cells provide fewer photons to the detectors resulting in a distinctly lower signal. This distinctly lower signal results in a noticeable separated subpopulation which allows the exclusion ("gating out") of the membrane compromised sperm during the sorting procedure. Since membrane compromised sperm comprises largely non-viable sperm, excluding these cells from the analysis results in an enriched sperm subpopulation with respect to viability in the sex sorted subpopulation.

In addition to the desired signal produced by chromosomal or nuclear DNA during sorting, non-specific florescence can be produced from viable sperm during the sorting process. Non-specific florescence may include florescence emissions not coming from the DNA-stain complex, such as auto-florescence from NADH and NADPH, stain that may have associated with mitochondrial DNA, stain that may have associated with RNA, and/or stain that may have associated with cellular lipophilic components. While the exact source of non-specific noise from viable sperm is not known with certainty, it was appreciated by applicants for the first time that this noise may be, at least partially, at a different wavelength that the signal of interest. Namely, non-specific noise may, at least partially, occur in the 520 nm to 600 nm wavelength range, or perhaps at about 520 nm. Certain embodiments of the present invention provide split enhancing dyes which are impedance matched to this non-specific noise. Such split enhancing dyes may help improve sorting signals and sort purities by enhancing the distinction between two sperm subpopulations.

In this way, staining procedures may be improved to enhance splits by reducing the non-specific fluorescence of live sperm with the addition of split enhancing dyes impedance matched to that non-specific fluorescence. Since non-specific florescence is not correlated with the sex chromosome of sperm cells, if non-specific florescence has a high CV (coefficient of variation), then it may contribute a "noise signal" to the CV of the populations of live X-chromosome bearing and Y-chromosome bearing sperm. Even if the non-specific florescence is very low (such as 0.05%-0.25% of total florescence) if variation is high, it may contribute significant variation, causing a reduction in the resolution between the two closely related sex populations, resulting in what is generally called a "poor split". The result of a poor split is a slower sorting process, or conversely a good split is deemed essential to a fast sorting process.

In one aspect the invention provides a method of selecting gender enriched populations of sperm including the steps of: (1) obtaining a population of sperm; (2) staining the population of sperm with a DNA selective dye, a dead quenching dye, and, in some cases, a split enhancing dye; and (3) sorting the stained population of sperm. Certain embodiments described herein relate to mixed dyes with enhance sorting properties, while other embodiments relate to improved dead quenching dyes that improve sort parameters, such as, sort speed and sort purity.

In the first step (1), a population of sperm is obtained. The population of sperm can be obtained in the form of neat semen, extended sperm, frozen thawed sperm or in combinations thereof. The population of sperm can be obtained at the same location as the remaining steps, or can be extended in an appropriate sperm buffer for transport to a sorting facility. The sperm can be maintained at room temperature, chilled, or even frozen in an appropriate buffer for later use.

The step of obtaining sperm can include obtaining a frozen or chilled straw from storage, or even pooling frozen or extended sperm.

The population of sperm can originate from mammals, such as a non-human mammals listed by Wilson, D. E. AND Reeder, D. M., *Mammal Species of the World*, Smithsonian Institution Press, (1993), the entire contents of which are incorporated herein by reference.

In the second step (2), the population of sperm is stained in a process which includes a DNA selective fluorescent dye, a dead quenching dye and in some cases a split enhancing dye. The population of sperm can include X-chromosome bearing sperm and Y-chromosome bearing sperm. Additionally, each of the X-chromosome bearing sperm and the Y-chromosome bearing sperm can include viable sperm and nonviable sperm. Viable sperm can be considered sperm with intact membranes while nonviable sperm can be considered sperm with compromised membranes. Viable sperm, in the appropriate dosage, will generally be capable of achieving fertilization in an artificial insemination, while nonviable sperm, or membrane compromised sperm, will be incapable of achieving fertilization in an artificial insemination or will have a greatly reduced ability to do so. However, some sperm capable of fertilization may have compromised membranes, and some sperm with intact membranes may be incapable of fertilization. The staining can take place in two distinct steps. In the first step, at least a portion of the population of sperm is incubated with a first staining buffer and a DNA selective fluorescent dye. The purpose of the first step is to stoichiometrically stain the DNA content of each cell in the sperm population. Hoechest 33342 is described in U.S. Pat. No. 5,135,759, for this purpose. However, other UV excitable dyes, as well as visible light excitable dyes, fluorescent polyamides, fluorescent nucleotide sequences, and sex specific antibodies could also be used for this purpose.

Sperm in its natural state is often not readily permeable to such dyes. In order to produce a uniform staining, the first step of staining can include incubating at least a portion of the sperm population at an elevated temperature in a first staining buffer at an elevated pH in addition to the dye. Examples of appropriate first staining buffers can be a TALP, TES-TRIS, TRIS citrate, sodium citrate, or a HEPES based medium, each described in WO2005/095960, incorporated herein by reference. An exemplary modified TALP described in WO2001/37655, incorporated herein by reference, is illustrated in Table 1.

TABLE 1

Modified TALP buffer

| Ingredient | Concentration |
|---|---|
| NaCl | 95.0 mM |
| KCl | 3.0 mM |
| NaHPO$_4$ | 0.3 mM |
| NaHCO$_3$ | 10.0 mM |
| MgCL$_2$ 6H$_2$O | 0.4 mM |
| Na Pyruvate | 2.0 mM |
| Glucose | 5.0 mM |
| Na Lactate | 25.0 mM |
| HEPES | 40.0 mM |
| bovine serum albumin | 3.0 mg/ml |

As one example, the population of sperm, or a portion of the population of sperm, could be diluted with the first buffer to between $640 \times 10^6$ and $40 \times 10^6$ sperm/ml, to between about $320 \times 10^6$ and $80 \times 10^6$ sperm/ml, or to about $160 \times 10^6$ sperm/ml in the first buffer. The DNA selective florescent dye can be added to the sperm suspended in the first buffer in a concentration of between about 10 µM and 200 µM; between about 20 µM and 100 µM, or between about 30 µM and 70 µM. The pH of the first buffer can be between about 6.8 and 7.9; about 7.1 and 7.6; or at about 7.4 in order to help ensure a uniform staining of nuclear DNA. Those of ordinary skill in the art will appreciate the pH can be elevated with the addition of NaOH and dropped with the addition of HCl.

The population of sperm can be incubated between 30-39° C., between about 32-37° C., or at about 34° C. The period of incubation can range between about 20 minutes and about an hour and a half, between about 30 minutes and about 75 minutes, or for about 45 minutes to about 60 minutes. As one example, the population of sperm can be incubated for about 45 minutes at 34° C. Even within a single species, sperm concentration and pH and other factors affecting stainability can vary from animal to animal. Those of ordinary skill in the art can appreciate minor variations for incubating sperm between species and even between breeds or animals of the same breed to achieve uniform staining without over staining a population of sperm.

At the end of the incubation period, when the DNA selective fluorescent dye has sufficiently saturated the population of sperm to differentiate X-chromosome bearing sperm from Y chromosome bearing sperm, a second step of staining can include a further dilution in a second staining buffer that contains one or more additional dyes. The one or more additional dyes can include a single dye for the purpose of permeating and quenching signals from membrane compromised sperm cells, as well as, for reducing signal noise. The one or more additional dyes can also include the combination of a dead quenching dye and a split enhancing dye. The term "dead quenching dye" can be understood to include dyes which differentially associate with membrane compromised sperm. It may be that these dyes enter membrane compromised sperm cells more easily because the membranes are breaking down or otherwise increasingly porous, but it may also be that dead quenching dyes readily enter all sperm cells and that healthy sperm cells act to pump dead quenching dyes out faster than membrane compromised sperm. In either case, the sperm cells with which the dead quenching dyes associate includes a large portion of dead and dying sperm cells, although not necessarily all dead and dying sperm cells.

In an alternative embodiment, the dead quenching dye and/or the split enhancing dye may be introduced with the first staining buffer having the DNA selective dye, or in both the first staining buffer and the second staining buffer.

The second buffer can be applied in an equal volume to half the current sperm concentration. Similarly, the volume of the second buffer can be selected to achieve a desired final concentration of sperm for further processing, such as between about $320 \times 10^6$ and $20 \times 10^6$ sperm/ml, between about $160 \times 10^6$ and $40 \times 10^6$ sperm/ml, or about $80 \times 10^6$ sperm/ml. The second buffer can have a pH coordinated to bring the overall pH back to an ideal pH for sperm. In the case of bovine, where the pH has been taken to 7.4 with the first buffer, the second buffer can be applied at 5.5 in order to bring the final pH back to 6.8. The specific pH can vary from species to species, but that those of skill in the art can determine appropriate sperm pH and coordinate the second buffer to achieve a particular desired pH. In another embodiment, the second buffer can have the same pH as the first buffer.

The second buffer can be selected as a buffer similar to the first buffer. The pH of the second buffer can be reduced with the addition of HCl. As one example, the modified TALP can be used with the addition of a dead quenching dye, a split enhancing dye and with the addition of egg yolk, for example 4% egg yolk.

Figure 2:
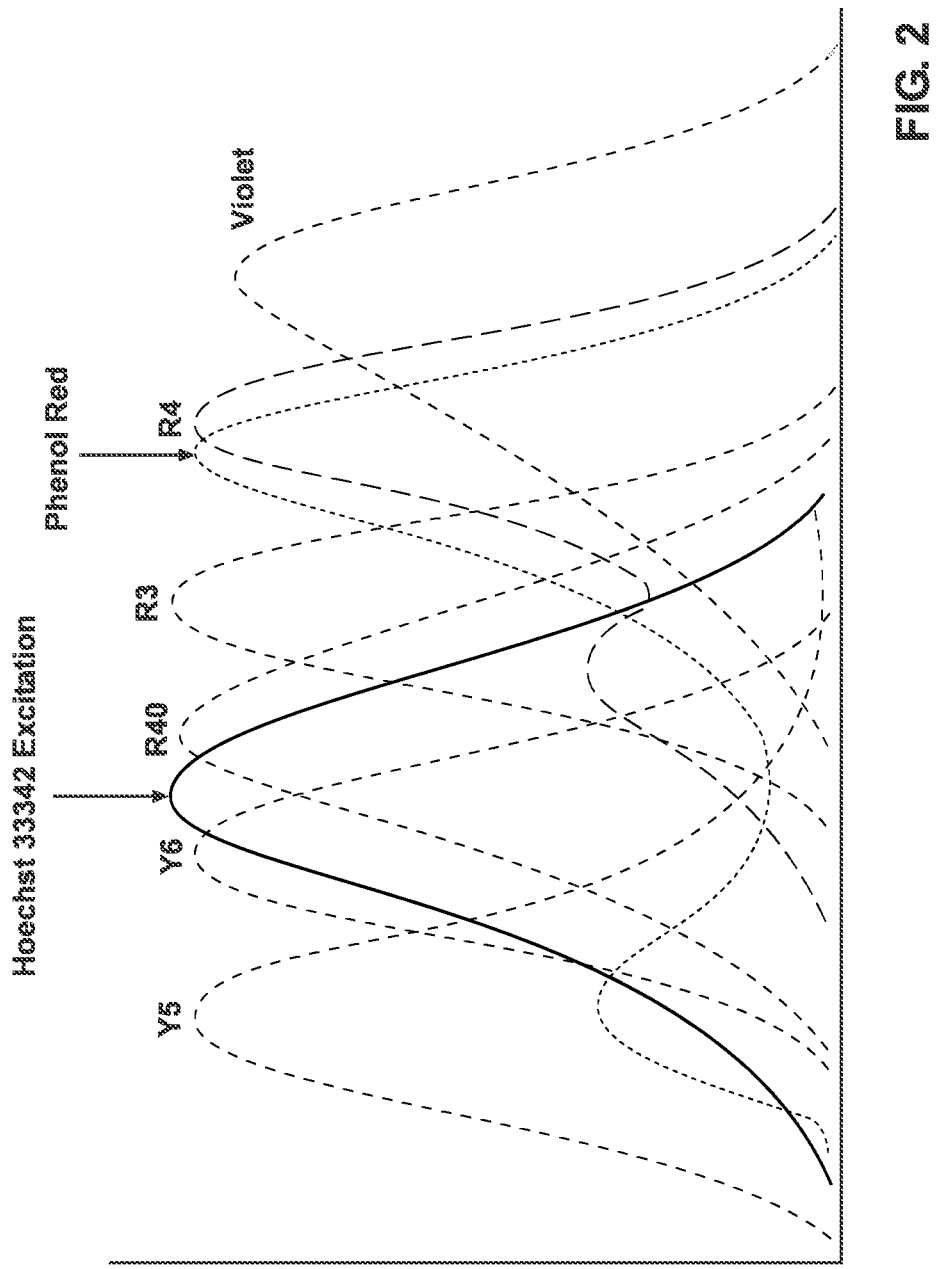
FIG. 2 illustrates an excitation curve for Hoechst 33342 as compared to absorption curves for several dyes.

The dead quenching dye can selectively quench the fluorescence of unwanted cells. To achieve this, the dye must enter unwanted cells and efficiently absorb the fluorescent emission of the DNA selective dye. In the case of sperm sorting, membrane compromised sperm are permeable to many dyes. Red food dye No. 40 was previously used for this purpose. However, improvements in quenching efficiency are possible where the dead quenching dye is impedance matched more closely to the excitation of the DNA selective fluorescent dye. In the case of sperm, a common DNA selective fluorescent dye is Hoechst 33342, described above, which is expected to fluoresce at a maximum emission at about 483 nm in the emission spectra. Improved quenching dyes may therefore be impedance matched to this emission value when they have corresponding absorption maximums at near the same value. Table 2 below illustrates several food dyes and their expected absorption maxima in water. Additionally, FIG. 2 provides a visual representation of the emission intensity of Hoechst 33342, when excited by a UV laser in comparison to the absorption spectra of yellow food dye No. 5 (Y5), yellow food dye No. 6 (Y6), red food dye No. 40 (R40), red food dye No. 3 (R3), red food dye No. 4 (R4), phenol red, and violet.

TABLE 2

Expected Absorption Maxima (nm)
of FD&C Dyes and Phenol Red

| Dye Maxima[a](nm) | Solvent | Absorption | |
|---|---|---|---|
| Yellow 5 | water | 422 | |
| Phenol Red | water | 440 | 560 |
| Yellow 6 | water | 480 | |
| Red 40 | water | 505 | |
| Red 2 | water | 520 | |
| Red 4 (natural) | water | 520 | 555 |
| Red 3 | water | 530 | |
| Blue 2 | water | 610 | |
| Green 3 | water | 625 | |
| Blue 1 | water | 627 | |

[a]The maxima will vary slightly due to variations in solvent.

Exemplary dead quenching dyes can be those having lower absorption maxima than red food dye No. 40. Such dyes may be visually characterized as yellow, orange, or orangish-red in color and may have absorption maxima in the range of between about 420 nm and about 500 nm. Exemplary dyes can include yellow dyes, such as FD&C yellow food dye no. 6, Disodium 6-hydroxy-5[(4-sulfophenyl)azo]-2-naphthalenesulfononate, (hereafter "yellow food dye no. 6" or "yellow 6"); and FD&C yellow food dye No. 5, Trisodium (4E)-5-oxo-1-(4-sulfonatophenyl)-4-[(4-sulfonatophenyl)hydrazono]-3-pyrazolecarboxylate, (hereafter "yellow food dye no. 5" or "yellow 5"). Both food dyes demonstrate an ability to quench membrane compromised sperm cells in the sex sorting process.

The dead quenching dye is selected for its ability to permeate membrane compromised sperm cells and to dampen the fluorescence produced by the DNA selective fluorescent dye in those cells. Some orange and yellow food dyes demonstrate an improved ability to differentiate membrane compromised sperm from healthier sperm. For example, yellow food dye No. 6 tends to exhibit superior quenching to previous dead quenching dyes. Yellow food dye No. 6 may permeate membrane compromised sperm more effectively, or may possess a greater ability to absorb photons. At the same time some yellow dyes demonstrate less dampening to the overall signal. These benefits allow for less DNA selective fluorescent dye with the first staining buffer and less yellow dye with the second staining buffer, as compared to the amount of red food dye No. 40 previously used.

As dead quenching dyes, yellow food dye No. 6 can be used in a concentration of greater than 12.5 µM, between 12.5 µM and 250 µM, or between 20 µM and 125 µM. Yellow food dye No. 5 can be used in concentrations greater than 125 µM, or between about 125 µM and 500 µM.

Exemplary split enhancing dyes can be red dyes other than red food dye no. 40, or perhaps even reddish and violet dyes. The local absorption maximum wavelength of split enhancing dyes may be greater than that of red food dye No. 40, namely greater than 505 nm. The local absorption maximum wavelength may be greater than about 520 nm. Alternatively, the split enhancing dye can have a local absorption maximum wavelength between about 520 nm and about 600 nm. Exemplary dyes can include phenol red, sometimes referred to as phenolsulfonphthalein or PSP; natural red food dye No. 4, known as carmine or natural red 4 (hereafter "carmine" or "red food dye No. 4"); and FD&C red food dye No. 3, 2-(6-Hydroxy-2,4,5,7-tetraiodo-3-oxo-xanthen-9-yl)benzoic acid, (hereafter "red food dye No. 3" or "red 3"). The examples below demonstrate phenol red and red food dye No. 4 as improving the split quality at a number of concentrations. Red food dye No. 3 also improves sorting at some concentrations. With reference to Table 2, Phenol red is believed to have a maximum absorption at about 560 nm to 570 nm (in the red molecular form), red food dye No. 4 is believed to have local maximum absorption wavelengths at 520 nm and 555 nm, while red food dye No. 3 has an absorption maximum at about 530 nm. Dyes having similar molecular weights and absorption maxima are expected also provide improvements in sorting. For example, dyes having local absorption maxima in the range of about 520 nm to about 600 nm, or about 530 nm to about 580 nm are expected to also provide improvements in the signal to noise ratio. Possible autofluorescence and other unintended fluorescence, such as possibly Hoechst 33342 bound to mitochondrial DNA may to emit in the spectral range of about 520-600 nm. Therefore, by impedance matching a split enhancing dye to have local absorption maxima at those wavelengths, noise can be reduced in the overall signal.

In some embodiments, the split enhancing dye can be used in addition to a dead quenching dye, while in other embodiments the split enhancing dye can double as a dead quenching dye. As one example, phenol red, red food dye No. 4, or red food dye No. 3 can be used as split enhancing dyes in combination with yellow food dye No. 6 for quenching membrane compromised sperm. Each of phenol red, red food dye No. 4, and red food dye No. 3 have surprisingly been found to reduce noise and enhance splits independent of dead quenching in sperm sorting.

Phenol red and red food dye No. 4 may be used as a split enhancing dye at concentrations between 0.1 µM, and 1200 µM, and between 5 µM and 620 µM, and between 15 µM and 125 µM. Red food dye No. 3 may be used as a split enhancing dye in concentrations between about 25 µM and 600 µM, and 150 µM and 600 µM.

In some embodiments split enhancing dyes may be used for quenching membrane compromised sperm, although they tend to be less efficient at doing so and require greater concentrations. For example, phenol red can be used for quenching membrane compromised sperm in concentrations between about 250 µM, and about 1250 µM.

In step (3) the stained population of sperm can be sorted, such as by flow cytometry. With reference to FIG. 1, a flow cytometer (10) is shown for sorting stained sperm. The flow cytometer (10) includes a cell source (12) supplying a sample for sorting. The sample includes the stained sperm, such as sperm stained with a DNA selective fluorescent dye and one or more other dyes. The stained sperm are deposited within a nozzle (14) and introduced into a fluid stream (16) of sheath fluid (18). The sheath fluid (18) can be supplied by a sheath fluid source (20) so that as the cell source (12) supplies the sperm into the sheath fluid (18) they are concurrently fed through the nozzle (14). In this manner the sheath fluid (18) forms a fluid stream coaxial to the sample having stained sperm. Since the various fluids are provided to the flow cytometer (10) at some pressure, they flow out of nozzle (14) and exit at the nozzle orifice (22). By providing an oscillator (24) which may be very precisely controlled through an oscillator control (26), pressure waves may be established within the nozzle (14) and transmitted to the fluids exiting the nozzle (14) at nozzle orifice (22). Since the oscillator (24) acts upon the sheath fluid (18), the fluid stream (16) exiting the nozzle orifice (22) eventually and regularly forms drops (28) at precise frequencies and velocities. Because the stained sperm are surrounded by the fluid stream (16) or sheath fluid environment, the drops (28) may contain within them individually isolated spermatozoa.

Since the drops (28) can contain individual spermatozoa, the flow cytometer can be used to sort sperm based upon individual cell characteristics. This is accomplished through a cell sensing system (30). The cell sensing system (30) includes at least a sensor (32) responsive to the cells contained within fluid stream (16). The cell sensing system (30) may cause an action depending upon the relative presence or relative absence of a characteristic. Certain characteristics, such as the relative DNA content of sperm cells, can be detected through excitation with an electromagnetic radiation source (34), such as a laser generating an irradiation beam to which the stained sperm are responsive. The electromagnetic radiation source (34) can be a laser operated at UV wavelength, such as at about 355 nm laser operated at 175 mW. Alternatively, a laser can be run at a higher power and split between several fluid streams.

The characteristics of individual sperm, particularly the presence of an X-chromosome or a Y-chromosome can be determined from the detected fluorescence produced in response to the electromagnetic radiation source (34). The DNA selective fluorescent dye binds stoichiometrically to sperm DNA. Because X-chromosome bearing sperm contain more DNA than Y-chromosome bearing sperm, the X-chromosome bearing sperm can bind a greater amount of DNA selective fluorescent dye than Y-chromosome bearing sperm. Thus, by measuring the fluorescence emitted by the bound dye upon excitation, it is possible to differentiate between X-bearing spermatozoa and Y-bearing spermatozoa.

In order to achieve separation and isolation based upon stained sperm characteristics, emitted light can be detected by the sensor (32) and the information fed to an analyzer (36) coupled to a droplet charger which differentially charges each drop (28) based upon the characteristics of the stained sperm contained within that drop (28). In this manner the analyzer (36) acts to permit the electrostatic deflection plates (38) to deflect drops (28) based on whether or not they contain the appropriate particle or cell.

As a result, the flow cytometer (10) acts to separate stained sperm by causing the drops (28) containing sperm to be directed to one or more collection containers (40). For example, when the analyzer differentiates sperm cells based upon a sperm cell characteristic, the droplets entraining X-chromosome bearing spermatozoa can be charged positively and thus deflect in one direction, while the droplets entraining Y-chromosome bearing spermatozoa can be charged negatively and thus deflect the other way, and the wasted stream (that is droplets that do not entrain a particle or cell or entrain undesired or unsortable cells) can be left uncharged and thus is collected in an undeflected stream into a suction tube or the like as discussed in U.S. patent application Ser. No. 09/001,394, hereby incorporated by reference herein. Naturally, numerous deflection trajectories can be established and collected simultaneously.

FIG. 3 illustrates comparisons of bivariate plots generated in sex sorting sperm which reflect the intensity of the excited DNA selective fluorescent dye during sorting. Three bulls were stained with equal amounts of Hoechst 33342 and with an equal amount of yellow food dye No. 6 and red food dye No. 40. The region labeled as R4 surrounds what is considered the "dead" sperm population, while the region R1 is centered on viable, oriented sperm. It can be seen that for each bull yellow food dye no. 6 provided superior quenching as for each bull the "dead" population, having the majority of the membrane comprised sperm, was pulled further away from the "live" population as compared to red food dye No. 40.

FIG. 4 illustrates an example bivariate plot and univariate histogram of the parameters measured during sex selection by a FACS on a flow cytometer. The relative intensity of the live, or non-membrane compromised sperm can be seen on the bivatiate plot having a height labeled "B," while the relative intensity of the quenched dead, or quenched membrane compromised sperm is labeled "A." The differences in magnitude of lines "A" and "B" demonstrate the degree to which a membrane compromised subpopulation of sperm is quenched and may be represented as a fraction or a percentage. Without a dead quenching dye, both populations of sperm would overlap to a large extent, with unpredictable variations in the dead sperm.

The univarite histogram demonstrates the number of counts at particular values in the flow cytometer. Each peak represents one of either X-chromosome bearing sperm, or Y-chromosome bearing sperm, with some overlap seen at the base. The amount of separation between the peaks can be characterized in a number of ways. Here the line is indicated at "C" provides an indication of the peak height, whereas "D" provides an indication of the magnitude for the valley separating the peaks. High "D" values and low "C" values would indicate minimal overlap in the subpopulations and excellent splits, whereas when the length of C and D are equal, there is effectively no split. Split quality may be characterized as a ratio of the distances indicated by C and D.

Example 1

Comparison of Dead Quenching Dyes for Post Thaw Motility Sperm Motility in Bovine Collection—

Sperm was collected from 10 different bulls on a routine collection schedule using an artificial vagina over the course of 4 days. The 10 bulls included both Jersey bulls and Holstein bulls. All ejaculates contained greater than 60% progressive motility and greater than 70% morphological normal sperm. Antibiotics were added within 15 minutes of collection.

Staining—

Red food dye treatment 40%—A reduced volume of red food dye No. 40 control was established. Sperm was diluted to $160 \times 10^6$ sperm per ml in a modified TALP buffer, as described in Table 1, at a pH of 7.4. Samples collected from Jersey bulls were incubated with 16 µl of Hoechst 33342 per 2 ml of sample for between 45 and 60 minutes at 34° C., while samples collected from Holstein bulls were incubated 17 µl of Hoechst 33342 per 2 ml of sample for between 45 and 60 minutes at 34° C. After incubation an equal volume of a second modified TALP was added reducing the concentration to $80 \times 10^6$. The second modified TALP includes the components described in Table 1 with the addition of 4% egg yolk, 40 µM red food dye No. 40 (20 g/L) and the pH dropped to 5.5 with HCl.

Yellow Food Dye Treatment—

Yellow food dye was included in a second group at an equal concentration. Sperm was diluted to $160 \times 10^6$ sperm per ml in a modified TALP buffer, as described in Table 1, at a pH of 7.4. Samples collected from Jersey bulls were incubated with 14 µl of Hoechst 33342 per 2 ml of sample for between 45 and 60 minutes at 34° C., while sample collected from Holstein bulls were incubated 15 µl of Hoechst 33342 per 2 ml of sample for between 45 and 60 minutes at 34° C. After incubation an equal volume of a second modified TALP was added reducing the concentration to $80 \times 10^6$. The second modified TALP includes the components described in Table 1 with the addition 4% egg yolk, 20 g/L yellow food dye No. 6 and a pH dropped to 5.5 with HCl.

Sorting—

Just prior to sorting, each sample was filtered though a 40 µm nylon mesh. Each sample was sorted with an MoFlo SX XDP (Beckman Coulter, Inc., CA USA) operating at 40 psi. A tris-citrate-fructose sheath fluid was used comprising Tris (hydroxymethyl) aminomethane (Sigma Chemical Co, St. Louis, Mo., USA) citric acid monohydrate (Sigma Chemical Co, St. Louis, Mo., USA) and fructose (Sigma Chemical Co, St. Louis, Mo., USA). Antibiotics were additionally added to the sheath fluid.

Unquenched sperm having the desired sex characteristics were collected into a single tube with a tris-egg yolk catch fluid and the remaining sperm was removed with waste. The tris-egg yolk catch fluid comprised 20% egg yolk, Tris (hydroxymethyl) aminomethane (Tris 200 mM; Sigma Chemical Co, St. Louis, Mo., USA), citric acid monohydrate (65 mM; Sigma Chemical Co, St. Louis, Mo., USA), fructose (56 mM; Sigma Chemical Co, St. Louis, Mo., USA) and antibiotics, where the sample remained for a maximum of approximately three hours.

Freezing—

Prior to freezing, the sorted sperm sample was cooled to about 5° C. and extended with a Tris-citrate-fructose solution similar to the catch fluid but additionally containing 12% glycerol. The cooled sorted sample was centrifuged and resuspended in a Tris-citrate-fructose solution with 20% egg yolk solution and 6% glycerol to arrive at a final concentration of $10 \times 10^6$ sperm/ml. Sperm was stored in divided into $2.1 \times 10^6$ doses and stored in 0.25 ml straws which were then cryopreserved with liquid nitrogen vapor.

Results—

Straws were thawed the following day for motility measurements at 0 hour and 3 hours. Percent intact acrosomes were measured as well, and the overall averages over all bulls on each day are illustrated in Table 3. Each bull tended to average higher post thaw motilies at 0 hour and at 3 hours as well as improved acrosomal integrity.

TABLE 3

| Post thaw Motility Bovine | |
|---|---|
| Motility | % |
| Average 0 Hour Red | 56.6% |
| Average 0 Hour Yellow | 57.7% |
| Average 3 Hour Red | 47.0% |
| Average 3 Hour Yellow | 49.0% |
| Average PIA Red | 70.8% |
| Average PIA Yellow | 71.3% |

Example 2

Comparison for Dead Quenching Dyes for Sorting Parameters in Bovine

Collection—

8 Sperm collections were taken from 7 different bulls on a routine collection schedule using an artificial vagina. The 7 bulls included both Jersey bulls and Holstein bulls. All ejaculates contained greater than 60% progressive motility and greater than 70% morphological normal sperm. Antibiotics were added within 15 minutes of collection. Portions of each collected sample received three different dead quenching dye treatments.

Staining—

Red food dye No. 40 treatment 100% (control)—A control was established with a conventional volume of red food dye No. 40. Sperm was diluted to $160 \times 10^6$ sperm per ml in a modified TALP buffer, as described in Table 1, at a pH of 7.4. Samples collected from Jersey bulls were incubated with 16 µl of Hoechst 33342 per 2 ml of sample for 60 minutes at 34° C., while sample collected from Holstein bulls were incubated 17 µl of Hoechst 33342 per 2 ml of sample for between 45 and 60 minutes at 34° C. After incubation, an equal volume of a second modified TALP was added reducing the concentration to $80 \times 10^6$. The second modified TALP includes the components described in Table 1 with the addition 4% egg yolk, 125 µM red food dye No. 40 and a pH dropped to 5.5 with HCl.

Red food dye No. 40 treatment 40%—A second group was prepared in the same way as the first, but with a 40% concentration of the red food dye No. 40, 50 µM red food dye No. 40.

Yellow food dye No. 6 treatment—Yellow food dye was included in the final group and was prepared in the same manner as Example 1. The concentration of yellow food dye No. 6 corresponds to the 40% red food dye No. 40 treatment at a concentration of 50 µM.

Sorting—

Just prior to sorting, each sample was filtered though a 40 µm nylon mesh. Each sample was sorted with a MoFlo SX XDP (Beckman Coulter, Inc., CA USA) operating at 40 psi. The sheath fluid described in Example 1 was used for sorting.

The event rate was held as close to 40,000 per second as possible for each sort and each sample was sorted for X-chromosome bearing sperm. The eight sorts were carried out on 6 different machines in order to minimize instrumentation effects and to average out differences in each instruments performance due to nozzle, beam shaping, and drop drive frequency.

Results—

In Tables 3-6 benefits to the sorting speed and sorting resolution are demonstrated with a reduced concentration of yellow food dye No. 6. Sperm samples quenched with yellow food dye No. 6 are denoted Y6. The control amount of red food dye No. 40 is identified as R40-100%, and R40-40% represents a red food dye No. 40 at a 40% concentration as compared to the control (125 µM vs. 50 µM).

Table 4 illustrates the average event rates across each sample and demonstrates they were maintained within just over 1%. Table 5 demonstrates a minor improvement in sort purity using a smaller amount of red food dye No. 40, and a further improvement in purity using yellow food dye No. 6, with a corresponding reduction in DNA selective fluorescent dye. Table 6 demonstrates a 14% increase in sort speed with the yellow food dye No. 6 is used as a dead quenching dye. This is a significant improvement given that the event rates were separated by only about 1% and that the sort purities were also very similar. Table 7 demonstrates that the X region contains 42.7% of the sperm population in the samples quenched with yellow food dye No. 6, as opposed to 39.1% and 38.4% for each of the red food dye quenchers. And this appears where yellow food dye No. 6 out performs the red food dyes. The improved resolution allows for excluding fewer cells which were not intended to be excluded resulting in a larger percentage of cells in sort region, and faster sort times at similar event rates.

As the sorting region and sorting speeds improve, Table 8 illustrates the number of coincident aborts also increase.

TABLE 4

AVERAGE EVENT RATE (events per second)

| R40 - 100% | 40412 |
|---|---|
| R40 - 100% | 40255 |
| Y6 | 40675 |

TABLE 5

AVERAGE PURITY (percent)

| R40 - 100% | 89.5 |
|---|---|
| R40 - 100% | 89.2 |
| Y6 | 90.5 |

TABLE 6

AVERAGE SORT SPEED (sorts per second)

| R40 - 100% | 5406 |
|---|---|
| R40 - 100% | 5522 |
| Y6 | 6194 |

TABLE 7

AVERAGE X REGION (percent)

| R40 - 100% | 38.4 |
|---|---|
| R40 - 100% | 39.1 |
| Y6 | 42.7 |

TABLE 8

AVERAGE ABORT RATE (aborts per second)

| R40 - 100% | 3310 |
|---|---|
| R40 - 100% | 3292 |
| Y6 | 3540 |

Example 3

Comparison of Dead Quenching Dyes for Sperm Motility in Deer and Elk

Collection—

Each of deer and elk were collected in the Tris-egg yolk catch fluid described as a catch media in Example 1, and shipped for sorting.

Staining—

A portion of each of the deer and the elk were stained by the red food dye No. 40 treatment 40% with 16 µL Hoechst 33342 and the yellow food dye No. 6 treatment with 14 µL Hoechst 33342 as described in Example 1.

Sorting and Freezing—

Samples were each bulk sorted with the same machine and parameters described in Example 1. Both sorted X and sorted Y sperm were collected into a single catch. The sorted samples were then frozen like those described in Example 1.

Results—

Frozen thawed samples were then tested for post thaw motilities and post thaw DNA fragmentation. Post thaw motilities were slightly higher in Elk sorted with a yellow quencher, while a more significant difference existed in progressive motility. In Table 10, post thaw DNA fragmentation in Elk can be seen at about double after 48 hours when red food dye No. 40 is compared to yellow food dye No. 6 as a dead quencher. In Tables 9 and 11, Deer and Elk each demonstrated improved motility and progressive motility in the samples quenched with yellow food dye No. 6 and stained with 14 µL of Hoechst 33342 as compared to the red food dye No. 40 with 16 µL of Hoechst 33342.

TABLE 9

Post Thaw Motility Elk

| | | Motile | Progressive |
|---|---|---|---|
| RED TALP, 16st | 0 HR | 51.0 | 29.0 |
| Y6, 14st | | 55.5 | 38.0 |

TABLE 10

Post Thaw DNA fragmentation Elk

| | | Pre-sort | Post Sort |
|---|---|---|---|
| RED TALP, 16st | 0 HR | 2.3 | 0.0 |
| | 24 HR | 5.6 | 0.3 |
| | 48 HR | 6 | 0.7 |
| Y6, 14st | 0 HR | 2.3 | 0.0 |
| | 24 HR | 3.3 | 0 |
| | 48 HR | 3.7 | 0.3 |

TABLE 11

Post Thaw Motility Deer

|  |  | Motile | Progressive |
|---|---|---|---|
| RED TALP, 16st | 0 HR | 59.8 | 43.0 |
| Y6, 14st |  | 67.5 | 53.2 |

Example 4

Comparison of Dead Quenching Dyes for Sperm Motility in Dog

Collection—

Sperm was collected from a single canine at room temperature into CaniPro Chill 5, available from Minitube, WI, USA, then centrifuged into a pellet and resuspended in a Tris buffer at a pH of 6.8.

Staining—

Samples were extended to $40 \times 10^6$ sperm/ml in 1 ml volumes with the Tris buffer described in Example 1 but set to a pH of 7.2. Ten samples were then stained 4, 4, 5, 5, 7, 8, 8, 9, 9, and 10 µL of Hoechst 33342 and quenched with one of two quenching dyes at a concentration of 50 µM in a second buffer Tris buffer.

Red food dye No. 40 quencher—1 ml Tris at a pH 6.3 was added with red food dye No. 40 into samples stained with 4, 5, 8, 9, 10 µL Hoechst 33342. The red food dye No. 40 was added at a concentration of about 50 µM.

Yellow food dye No. 6 quencher—1 ml Tris at a pH 6.3 was added with yellow food dye No. 6 into samples stained with 4, 5, 7, 8, 9 µL Hoechst 33342. The yellow food dye No. 6 was added at the same concentration as the red food dye No. 40 quencher, at about 50 µM.

After quenching, each sample had a total volume of 2 mL.

Sorting—

5 million cells were sex sorted with a MoFlo SX XPD into 50 mL Falcon tubes having 3.5 mL of a Tris-egg yolk catch fluid, described in Example 1 for both X and Y populations. Two samples were sorted, the red food dye No. 40 quenched treatment with 9 µL Hoechst 33342 and the yellow food dye No. 40 quenched treatment with 7 µL Hoechst 33342.

On the sorter, the samples sorted with red quenched treatment with 9 µL Hoechst 33342 demonstrated 50.73 percent of sperm in the X region and 8.92 percent were gated as dead. Samples sorted with the yellow quencher had 48.7 percent of sperm in the X region and only 4.42 percent of the sperm gated as dead.

Freezing—

Straws were then frozen and stored in liquid nitrogen.

Thawing—

Straws were thawed for 30 sec in a 38° C. water bath and their motilities were examined on CASA.

Results—

Table 12 illustrates the average motilities and progressive motilities for the sorted treatments. Canine sperm quenched with yellow food dye No. 6 provided about 4.5% more motile sperm in the X population and 6.5% more motile sperm in the Y population. Similarly, the yellow quenched dye provided 7% better progressive motility in the X population and 8% better progressive motility in the Y population.

TABLE 12

Dead quenching dye motilities

|  | TIME | Total cells | Motile | Progressive |
|---|---|---|---|---|
| X YELLOW 6 AVERAGE | 0 Hr | 192 | 24 | 18.5 |
| Y YELLOW 6 AVERAGE | 0 Hr | 322 | 25 | 21 |
| X RED TALP AVERAGE | 0 Hr | 312 | 19.5 | 11.5 |
| Y RED TALP AVERAGE | 0 Hr | 328 | 18.5 | 13 |

Example 5

Comparison of Dead Quenching Dye Amounts Vs Hoechst 33342 Stain Amounts

Collection—

A single Jersey bull was collected at an initial sperm concentration $1900 \times 10^6$ sperm/ml in a volume of 5 ml. The progressive motility of the sperm was 65% with normal morphologies greater than 65%.

Staining—

The entire ejaculate of sperm was suspended in first staining buffer, specifically a 7.4 pH TALP described in TABLE 1, to a concentration of $160 \times 10^6$ sperm per mL (determined on nucleocounter) and divided into three aliquots of about 20 mL into 50 mL Falcon tubes and pre-warmed for 10 minutes at 34° C. The DNA selective fluorescent dye, Hoechst 33342, was added and samples were held at 34° C. for 60 minutes. 3 different Hoechst 33342 Stain Levels were used=12 µL, 14 µL and 16 µL per 2 mL (effective concentrations of 48 µM, 56 µM, 64 µM).

Preparation of the second buffer including the dead quenching dye—A 2 L bag of TALP, described in TABLE 1, was adjusted to pH 5.60 using HCl and then sterile filtered. (Note: This test did not use 0.3% v/v BSA or 4% v/v Egg Yolk in the second buffer). For each of the four dyes tested (R40-red food dye No. 40, Y5—yellow food dye No. 5, Y6—yellow food dye No. 6 and PR—phenol red), an appropriate number of milligrams of each powder was placed in a Erlenmeyer Flask and then an exact amount of TALP pH 5.60 was added to create a 250 µM concentration of the dye. The result was a working TALP stock for each dye with a 100% (125 µM) relative amount of dye 50% relative (62.5 µM) and 20% relative (25 µM) solutions were made by dilution of 100% by TALP pH 5.60.

Controls—

Single tubes of stained sperm at each of the three Hoechst 33342 concentrations were treated with TALP pH 5.60 which had no dead quenching dye present. Single tubes using Vitamin B12 (red colored chemical) with stock concentration of 15 µM (12% relative) were tested.

Sorting and Data Acquisition—

After this "bulk" staining for 60 minutes, 1 mL aliquots of stained sperm were combined with 1 mL aliquots of the second buffer including the dead quenching dyes. Samples sat for approximately 30 minutes at room temperature before being analyzed on a MoFlo SX (Beckman Coulter, USA) sperm sorting flow cytometer. Event rates were held as close to 13,000 as possible at the point of data acquisition.

The total number of individual treatments was 42 tubes, each containing 2 mL of stained sample. The alignment of the sorter was established using nuclei and confirmed with live sample from the 50% Red 40 series. Once good alignment was established, each tube was placed on the sorter long enough to establish a stabile dead gate population (about 30 seconds) and then a screenshot was taken and saved as a .jpeg image. This approach of rapidly documenting each sample is used to assure the most consistent alignment between all samples. Realignment of sorter will not cause differences in the intensities of live and dead gate populations but will cause differences in split quality.

ordered as red food dye No. 40 and yellow food dye No. 6 being about equal and better than the remaining dyes. Of the remaining dyes yellow food dye No. 5 had better quenching properties than phenol red. From the split quality data, food dye improves the quality of split compared to no food dye control. Relative level of 20% food dye might be better than 40%.

TABLE 13A dead quenching and split enhancing capacities

| Hoechst | No stain | Red 40 | | | Yellow 6 | | |
|---|---|---|---|---|---|---|---|
| μL/2 mL | 0 | 125 μM | 62.5 μM | 25 μM | 125 μM | 62.5 μM | 25 μM |
| | | Dead Intensity | | | | | |
| 16 | 100% | 35% | 50% | 65% | 40% | 52% | 70% |
| 14 | 100% | 41% | 53% | 72% | 40% | 52% | 74% |
| 12 | 100% | 37% | 53% | 68% | 37% | 50% | 68% |
| Average | 100% | 38% | 52% | 68% | 39% | 51% | 71% |
| | | Height of Peak/Height of Valley | | | | | |
| 16 | 1.00 | 1.21 | 1.00 | 1.00 | 1.26 | 1.00 | 1.13 |
| 14 | 1.44 | 2.00 | 1.62 | 1.94 | 1.80 | 1.62 | 2.07 |
| 12 | 1.50 | 1.75 | 1.65 | 2.05 | 1.73 | 1.70 | 2.05 |
| Average | 1.47 | 1.88 | 1.64 | 2.00 | 1.77 | 1.66 | 2.06 |

TABLE 13B dead quenching and split enhancing capacities

| Hoechst | Yellow 5 | | | Phenol Red | | | B12 |
|---|---|---|---|---|---|---|---|
| μL/2 mL | 125 μM | 62.5 μM | 25 μM | 125 μM | 62.5 μM | 25 μM | 0.25 |
| | Dead Intensity | | | | | | |
| 16 | 55% | 70% | 90% | 78% | 80% | 90% | 100% |
| 14 | 63% | 77% | 90% | 80% | 90% | 97% | 100% |
| 12 | 54% | 74% | 90% | 80% | 90% | 94% | 100% |
| Average | 57% | 74% | 90% | 79% | 87% | 94% | 100% |
| | Height of Peak/Height of Valley | | | | | | |
| 16 | 1.03 | 1.00 | 1.00 | 1.00 | 1.00 | 1.00 | 1.00 |
| 14 | 1.92 | 1.70 | 1.54 | 1.75 | 1.87 | 1.65 | 1.62 |
| 12 | 1.72 | 1.60 | 1.90 | 1.49 | 1.62 | 1.82 | 1.61 |
| Average | 1.82 | 1.65 | 1.72 | 1.62 | 1.75 | 1.74 | 1.62 |

Results—

FIG. 4 illustrates an example histogram. The ratio of dead gate intensity divided by live gate intensity is created by dividing the distance "A" by the distance "B" shown as a percentage. Lower values mean higher levels of quenching. The ratio of peak height divided by valley height is created by dividing the distance "C" by the distance "D". A value of 1.00 means "no split" while higher values mean "better splits".

Figure 5:
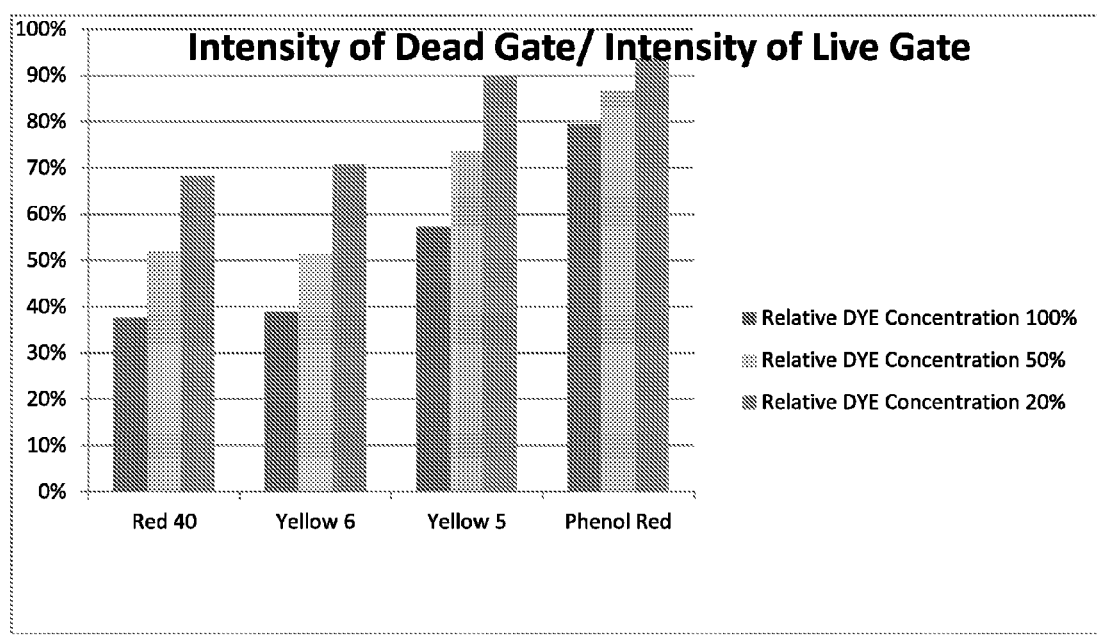
FIG. 5 illustrates a graphical comparison of the quenching capacity of various dyes as dead quenching dyes.
Figure 6:
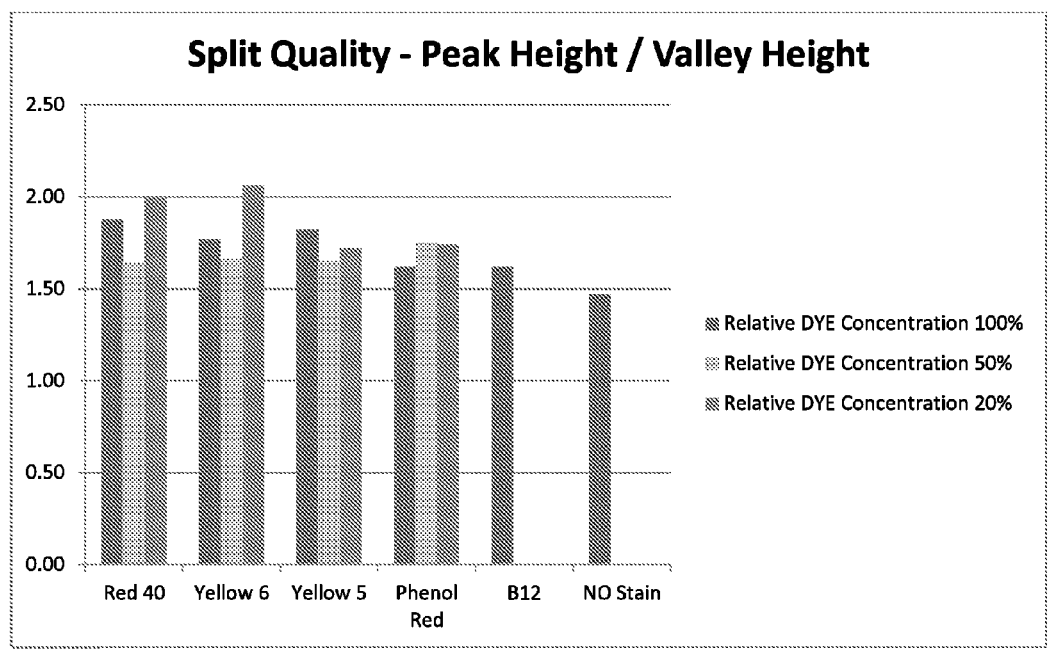
FIG. 6 illustrates a graphical comparison of the split quality produced when sorting with various dyes.

TABLE 13 shows the ratios created by making this measurement on each of 42 histograms generated in the data acquisition described above. 16 μL data was omitted in the split data of TABLE 13 because there was mostly no split in nearly all samples (due to "overstained condition"). FIG. 5 shows the average data for dead gate intensity divided by live oriented gate intensity. FIG. 6 illustrates the average data for 12 μL and 14 μL stain series for the height of peak divided by height of valley.

From the dead and live intensity data, the absorption of the four dyes (ability to create a dead gate population) is Example 6

Comparison of Dead Quenching Dye for Yellow Food Dye No. 6 and Phenol Red

Collection—

A single Jersey bull was collected at an initial sperm concentration $1810 \times 10^6$ sperm/ml in a volume of 3.9 ml. The progressive motility of the sperm was 65% with normal morphologies greater than 50%.

Staining—

Sperm were suspended at 320 million per mL in 30 mL a first buffer, (TALP described in table 1 at a pH 7.4) with 12 μL of Hoechst 33342 per 2 mL (48 μM) of stain and incubated for 1 hour at 34° C. Stained sperm was then placed as 1 mL aliquots in sample tubes and a 1 mL volume of the appropriate TALP was added. The same second buffer was used as example 1, namely a modified 5.60 pH TALP. Since the color, and hence the absorption characteristics of phenol red is pH sensitive, it was made in a first series with TALP pH 5.60 resulting in a pH of 6.70 (like example 1) and in a second series the second buffer had a pH of 7.40 (the same buffer as the first buffer, with the addition of the quenching dyes).

Sorting and Data Acquisition—

Each of the stained samples was sorted on a MoFlo SX (Beckman Coulter, USA) as described in Example 6. Screen shots were taken and the dead gate intensity and the split quality were measured in the same way described in Example 1 and recorded in TABLE 14.

TABLE 14

| | Phenol Red | | | | | | |
|---|---|---|---|---|---|---|---|
| | Yellow 5 | | | | | | Red 40 |
| | 1250 µM | 875 µM | 750 µM | 500 µM | 250 µM | 125 µM | 62.5 µM |
| Intensity | <30% | <30% | <30% | 43% | 48% | 63% | 53% |
| PV | 1.00 | 1.00 | 1.00 | 1.00 | 1.00 | 1.00 | 1.00 |
| | Phenol Red (pH 6.70) | | | | | | Yellow 6 |
| | 1250 µM | 875 µM | 750 µM | 500 µM | 250 µM | 125 µM | 62.5 µM |
| Intensity | 41% | 45% | 55% | 67% | 70% | 79% | 50% |
| PV | 1.29 | 1.20 | 1.25 | 1.25 | 1.17 | 1.00 | 1.00 |
| | Phenol Red (pH 7.40) | | | | | | |
| | 1250 µM | 875 µM | 750 µM | 500 µM | 250 µM | 125 µM | |
| Intensity | 43% | 47% | 56% | 66% | 76% | 85% | |
| PV | 1.30 | 1.44 | 1.46 | 1.51 | 1.22 | 1.27 | |

Results—

Figure 7A:
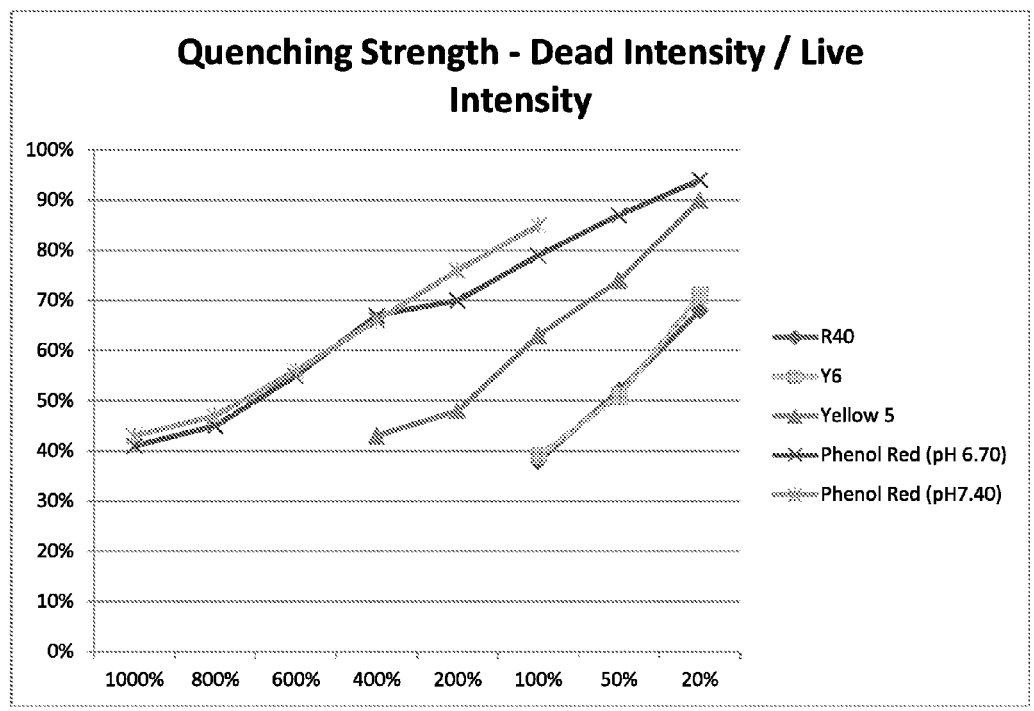
FIG. 7A illustrates a graphical comparison of the quenching capacity of various dyes as dead quenching dyes.

From the additional data on the proportional intensity of the dead gate it can be seen that it takes about five times as much yellow food dye No. 5 to get a similar dead gate intensity ratio as for red food dye No. 40 and yellow food dye No. 6. Furthermore, phenol red at both of the pH settings tested, is far less capable of quenching to create a dead gate, requiring twelve times more than red food dye No. 40 and yellow food dye No. 6. With respect to the ability to efficiently make a dead population, phenol red does not appear to be a good candidate, compared to red food dye No. 40 and yellow food dye No. 6 or yellow food dye No. 5. FIG. 7A illustrates a comparison of the concentrations required to achieve dead gates with each of the tested dye, combining the date from example 6 and example 7. It can be seen yellow food dye No. 6 and red food dye No. 40 perform similarly with respect to creating a dead gate, but that yellow food dye No. 5 and phenol red require significantly higher concentrations to affect a gate dead, or membrane compromised sperm.

Nonetheless, phenol red was the only of these four dyes which created a split improvement in this sample. This sample was "understained" at 12 µL/2 mL, meaning that there was either not enough Hoechst 33342 for uniform staining Because of this, the control samples did not have a split. It was very surprising, therefore, to see splits emerge in the presence of phenol red. Also, the quality of the split was improved by the higher pH TALP. At basic pH, phenol red (pKa 8.0) turn to an ionic alkaline form and exhibits a pink-red color.

Figure 7B:
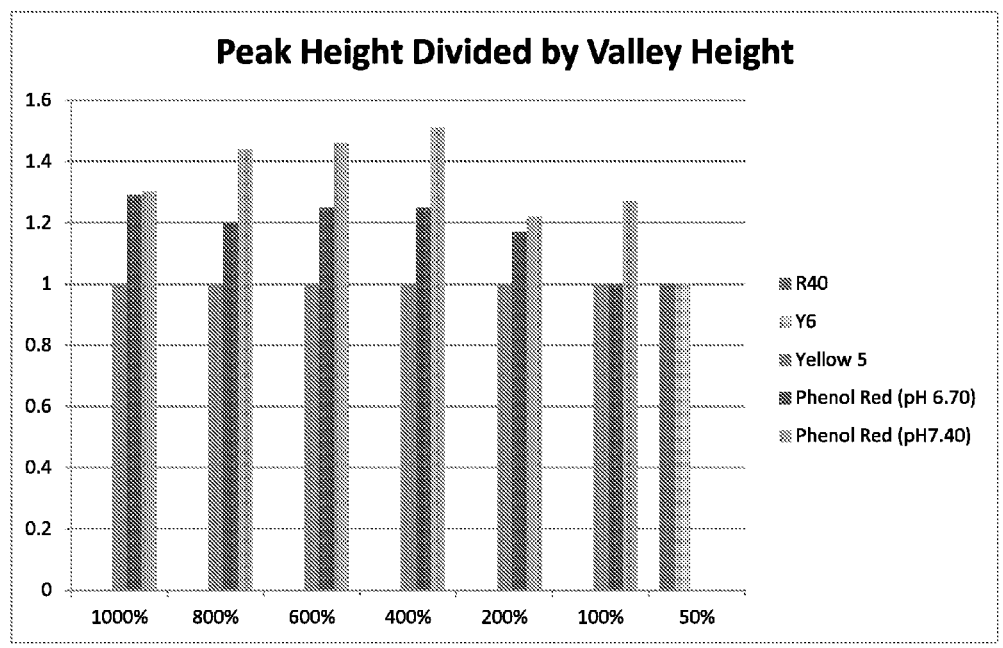
FIG. 7B illustrates a graphical comparison of the split quality produced when sorting with various dyes.

Keeping in mind a value of 1.00, is the equivalent of no split, the data in FIG. 7B is surprising in that splits emerge at all tested concentrations of phenol red. It appears that, especially at the higher pH configuration, phenol red acts to reduce noise and may be able to perform as a split enhancing dye.

Example 7

The Combined Effects of an Improved Dead Quenching Dye and a Split Enhancing Dye Collection—

A single Jersey bull was collected at an initial sperm concentration $1810\times10^6$ sperm/ml in a volume of 3.9 ml. The progressive motility of the sperm was 65% with normal morphologies greater than 50%.

Staining—

Sperm were stained in previously described first buffer TALP (pH 7.4) (described in TABLE 1 and in Example 1) at 160 million sperm/mL with the addition of 48 µM Hoechst 33343 (12 µL/2 mL) and 62 µM yellow food dye No. 6 and incubated for 1 Hour at 34° C. The sperm sample was then concentrated by centrifugation and resuspended at concentrations of 100, 150, 250, and 300 million sperm per mL, respectively. Samples were split into two equal aliquots and in one of each pair of samples, a stock solution of phenol red was added to make a final phenol red concentration of 620 µM. Samples at each concentration were prepared with the dead quencher yellow food dye No. 6 at a concentration of 62 µM. At each concentration, one control was compared to the addition of phenol red as a split enhancing dye at a concentration of 620 µM.

Sorting and Data Acquisition—

Sorting was performed on a MoFlo SX (Beckman Coulter, USA) in substantially the same manner described in Example 5. After calibration, screen shots of sorting histograms were taken and split quality was measured by the peak to valley ration in the same way described in Example 5. The resulting data is found in Table 15.

TABLE 15

| Phenol Red | | | |
|---|---|---|---|
| Concentration of Cells (million per mL) | Concentration of Yellow 6 (µM) | Concentration of Phenol Red (µM) | Height of Peak Divided by Height of Valley |
| 100 | 62 | 0 | 1.26 |
| 100 | 62 | 620 | 1.49 |

TABLE 15-continued

Phenol Red

| Concentration of Cells (million per mL) | Concentration of Yellow 6 (µM) | Concentration of Phenol Red (µM) | Height of Peak Divided by Height of Valley |
|---|---|---|---|
| 150 | 62 | 0 | 1.30 |
| 150 | 62 | 620 | 1.34 |
| 250 | 62 | 0 | 1.25 |
| 250 | 62 | 620 | 1.43 |
| 300 | 62 | 0 | 1.23 |
| 300 | 62 | 620 | 1.36 |

Results—

At each sperm concentration tested the combination of the split enhancing dye, phenol red, with the dead quenching dye, yellow food dye No. 6, gives better peak quality than the dead quencher at the concentrations of yellow food dye No. 6 tested.

Example 8

Phenol Red as an Added Split Enhancing Dye

Collection—

Two bulls were collected for the Example 8. The Bull 1 was a Jersey bulls and Bull 2 was a Holstein collected substantially in the manner described in example 1.

Staining—

Sperm from Bull 1 extended to 160 million per with a first buffer, (TALP described in table 1 at a pH 7.4) and divided into two groups for staining. The first group was stained with 44 µM Hoechst 33342 and the second group was stained with 60 µM Hoechst 33342. Similarly, bull 2 was suspended to 160 million per mL the first buffer, (TALP described in table 1 at a pH 7.4) and divided into three groups for staining. The first group was stained with 28 µM Hoechst 33342 and the second group was stained with 44 µM Hoechst 33342 and the third group was stained with 66 µM Hoechst 33342. Each group was incubated for 1 hour at 34° C. and then extended in an equal volume of the second buffer. The same second buffer was used as Example 1, namely a modified 5.60 pH TALP.

The stained samples were each treated with a variety of quenching dyes and combinations of quenching dyes indicated in below. Table 16 provides parings of results where phenol red is investigated in several concentrations, alone and in combination with red food dye No. 40 and yellow food dye No. 6, for comparison against a control lacking only the phenol red.

Sorting and Data Acquisition—

Sorting was performed on a MoFlo SX (Beckman Coulter, USA) in substantially the same manner described in Example 5. After calibration, screen shots of sorting histograms were taken and histograms split quality was measured as a peak to valley ratio in the same way described in Example 5 with reference to FIG. 4 and the resulting data is found in Table 16.

Results—

At each staining level of the DNA selective fluorescent dye, with both dead quenching dyes (Red 40 and Yellow 6), the addition of phenol red always improved split quality.

TABLE 16

Phenol Red as a split enhancing dye

| Bull | Conc Hoechst 33342 (µM) | Conc R40 (µM) | Conc Y6 (µM) | Conc PR (µM) | PV |
|---|---|---|---|---|---|
| Bull 1 | 44 | 0 | 0 | 0 | 1.44 |
| Bull 1 | 44 | 0 | 0 | 500 | 1.97 |
| Bull 1 | 44 | 0 | 50 | 0 | 1.20 |
| Bull 1 | 44 | 0 | 50 | 250 | 1.52 |
| Bull 1 | 60 | 0 | 0 | 0 | 1.60 |
| Bull 1 | 60 | 0 | 0 | 375 | 2.38 |
| Bull 1 | 60 | 20 | 0 | 0 | 1.62 |
| Bull 1 | 60 | 20 | 0 | 1200 | 2.12 |
| Bull 1 | 60 | 0 | 50 | 0 | 1.39 |
| Bull 1 | 60 | 0 | 50 | 375 | 2.38 |
| Bull 2 | 28 | 0 | 0 | 0 | 1.63 |
| Bull 2 | 28 | 0 | 0 | 375 | 1.96 |
| Bull 2 | 28 | 0 | 50 | 0 | 1.64 |
| Bull 2 | 28 | 0 | 50 | 375 | 2.05 |
| Bull 2 | 44 | 20 | 0 | 0 | 1.54 |
| Bull 2 | 44 | 20 | 0 | 375 | 1.64 |
| Bull 2 | 44 | 0 | 50 | 0 | 1.35 |
| Bull 2 | 44 | 0 | 50 | 225 | 1.56 |
| Bull 2 | 44 | 0 | 50 | 375 | 1.75 |
| Bull 2 | 60 | 0 | 50 | 0 | 1.35 |
| Bull 2 | 60 | 0 | 50 | 375 | 1.69 |
| Bull 2 | 60 | 0 | 375 | 0 | 1.72 |
| Bull 2 | 60 | 0 | 375 | 375 | 2.31 |

Example 9

Red Food Dye No. 3 as an Added Split Enhancing Dye

Collection—

A single bull was collected for the Example 9 in the same way described in Example 5.

Staining—

Sperm from Bull 1 extended to 160 million per with a first buffer, (TALP described in table 1 at a pH 7.4) and stained with 60 µM Hoechst 33342, as described in Example 1 at 34° C. for an hour. Each sample was then extended in an equal volume the second buffer, 5.6 pH modified TALP described in Example 5.

The second buffer also included either the dead quenching dye yellow food dye No. 6, or red food dye No. 40 at a concentration of 60 µM. The second buffer was additionally treated with concentrations of 25, 50, 100, 150, 300, or 600 µM of red food dye No. 3, as indicated in Table 6.

Sorting and Data Acquisition—

Sorting was performed on a MoFlo SX (Beckman Coulter, USA) in substantially the same manner described in Example 6. After calibration, screen shots of sorting histograms were taken and the split quality was measured in terms of peak to valley ratios in the same way described in Example 5 with reference to FIG. 4 and the resulting data is found in Table 17.

Results—

For each sample tested in Table 17, increasing concentrations or red food dye No. 3 improved the split quality up to the concentration of 300 µM. At a concentration of 600 µM the split enhancer red food dye No. 3 still provided improved splits compared to the control (0 red food dye No. 3), but not compared to a concentration of 300 µM.

TABLE 17

Red food dye No. 3 as a split enhancing dye

| Bull | Conc Hoechst 33342 (μM) | Conc R40 (μM) | Conc Y6 (μM) | Conc R3 (μM) | PV |
|---|---|---|---|---|---|
| Bull 3 | 60 | 0 | 50 | 0 | 1.26 |
| Bull 3 | 60 | 0 | 50 | 25 | 1.45 |
| Bull 3 | 60 | 0 | 50 | 100 | 1.38 |
| Bull 3 | 60 | 0 | 50 | 150 | 1.41 |
| Bull 3 | 60 | 0 | 50 | 300 | 1.66 |
| Bull 3 | 60 | 0 | 50 | 600 | 1.31 |
| Bull 3 | 60 | 0 | 50 | 0 | 1.32 |
| Bull 3 | 60 | 0 | 50 | 50 | 1.33 |
| Bull 3 | 60 | 0 | 50 | 100 | 1.55 |
| Bull 3 | 60 | 0 | 50 | 300 | 1.68 |
| Bull 3 | 60 | 0 | 50 | 600 | 1.42 |
| Bull 3 | 60 | 50 | 0 | 0 | 1.44 |
| Bull 3 | 60 | 50 | 0 | 50 | 1.63 |
| Bull 3 | 60 | 50 | 0 | 100 | 1.65 |
| Bull 3 | 60 | 50 | 0 | 200 | 1.78 |
| Bull 3 | 60 | 50 | 0 | 300 | 2.15 |

Example 10

Split Enhancing Dyes at Various Concentrations

Collection

Eight bulls were collected, including 4 Jersey bulls, 3 Holstein bulls and one mixed dairy-breed. The ejaculates were collected at concentrations ranging from $1700 \times 10^6$ sperm/ml to $1100 \times 10^6$ sperm/ml and all had progressive motility of a least 60%.

Staining—

Sperm from each bull was extended to 160 million per ml with a first buffer, (TALP described in table 1 at a pH 7.4) and stained with 64 μM (164/2 mL) Hoechst 33342 at 34° C. Additionally, Phenol Red, Red Food Dye No. 2, Red Food Dye No. 3, and Red Food Dye No. 4, were each tested as split enhancing dyes in the first buffer at concentrations of 15 μM, 45 μM and 125 μM. For each bull, each concentration of each dye was incubated for periods of 30 minutes, 45 minutes, 60 minutes, and 75 minutes were utilized before a second buffer with an additional dye was applied.

Each sample was then extended in an equal volume of a second buffer which comprised a 5.5 pH modified TALP having 25 μM yellow food dye No. 6 (acting as a dead quenching dye) in addition to the split enhancing dye provided in the first buffer. The second buffer was applied to every sample at 30 minutes, 45 minutes, 60 minutes, and 75 minutes. A control was additionally taken without any split enhancing dye for every bull at every time interval.

Sorting and Data Acquisition—

Sorting was performed on a MoFlo SX (Beckman Coulter, USA) in substantially the same manner described in Example 5. After calibration, screen shots of sorting histograms were taken and split quality was measured by peak to valley ratios in the same way described in Example 5 with reference to FIG. 4 and the resulting data, averaged over all 8 bulls, is found in Tables 18-21. Additionally, screen shots of bivariate plots were taken to measure the added dead quenching capacity of the mixed dead quenching and split enhancing dyes.

Results—

Figure 8:
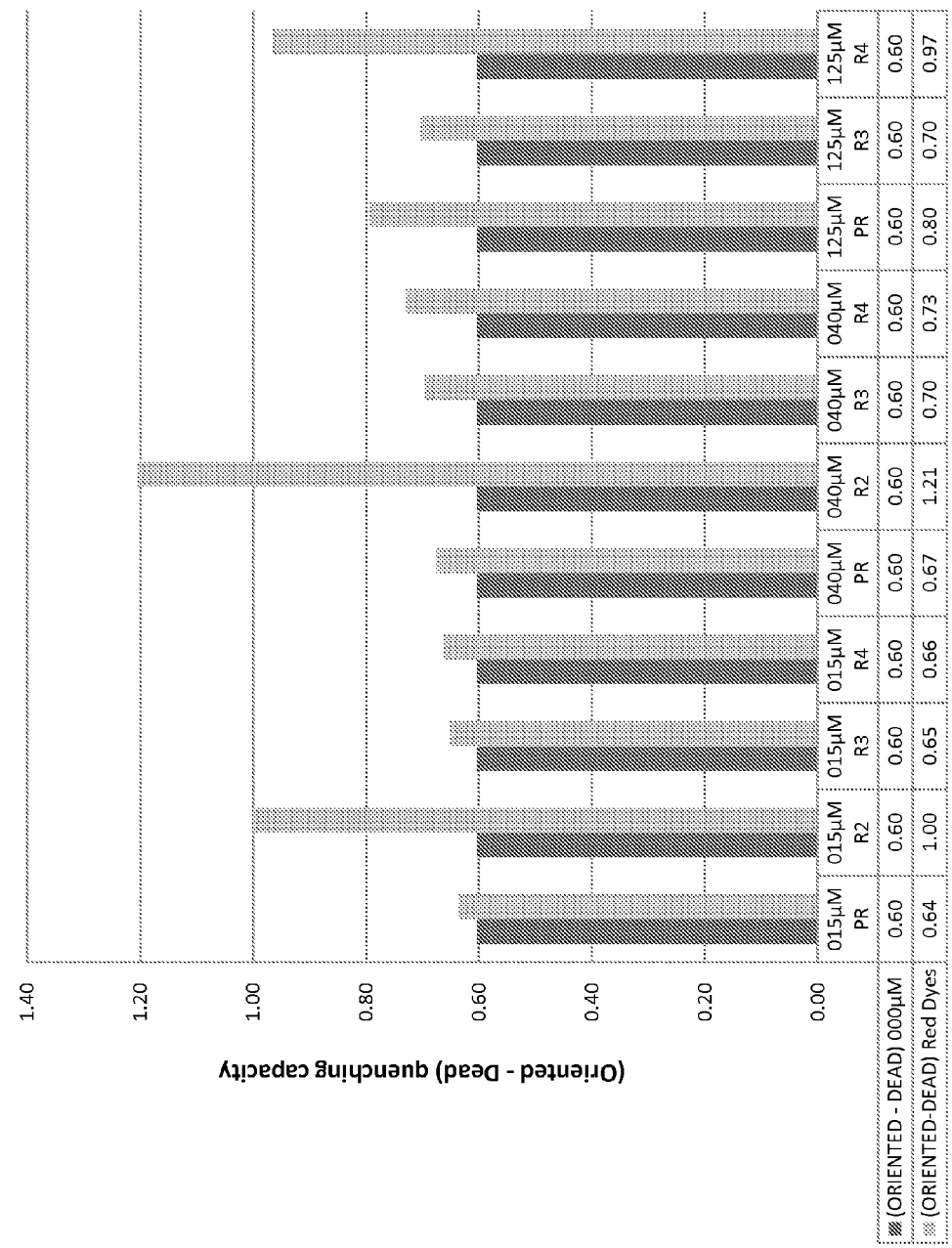
FIG. 8 illustrates a graphical comparison of the quenching capacity of various split enhancing dyes used in combination with a dead quenching dye.

Referring to Table 18, red food dye No. 2 did not provide a split enhancing, or noise reducing effect. Instead, averaged over the 8 bulls, every concentration of Red Food dye no. 2 resulted in a reduced peak to valley ratio, as compared to a control. Red food dye No. 2 did, however, provide a strong dead quenching capacity as seen in FIG. 8.

Referring to Table 19, red food dye No. 3, on average, provided initial split enhancements at 15 μM and 45 μM, but the control was as good as 45 μM after 60 minutes and as good as 15 μM after 75 minutes.

Referring to Table 20, Phenol Red provided consistent split improvements at all concentrations after 30 minutes. This improvement may provide a means for shortening incubation times, or may simply provide for higher throughput and higher purity in sex sorting protocols.

Referring to Table 21, red food dye No. 4 provides distinct improvements at all concentrations and at all times. Referring to FIG. 9, the split enhancement can be at each of 15 μM, 45 μM and 125 μM, particularly at 45 minutes and beyond. Red Food dye no. 4 may provide noise reduction and split enhancement at lower concentrations approaching 0 μM and does not show any sign of tailing off at the top end of the range tested. Red food dye No. 4 provided more consistent improvements across concentrations and times than phenol red and it is believed may continue to provide benefits in the ranges in which Phenol Red was tested in Example 9, such as concentrations as high as 1200 μM.

At the highest tested concentration red food dye No. 4 additionally provided a significant increase in quenching the dead subpopulation. Red food dye No. 4 may provide for a robust split enhancing dye over a large range of concentrations, and more provide the added benefit of reducing the amount of dead quenching dye required for sorting sperm.

TABLE 18

Red Food Dye No. 2 - Average 8 bulls

|  | 30 Min | 45 Min | 60 Min | 75 Min |
|---|---|---|---|---|
| Control - 0 μM Red 2 | 1.07 | 1.23 | 1.58 | 1.80 |
| 15 μM Red 2 | 1.06 | 1.15 | 1.54 | 1.73 |
| 45 μM Red 2 | 1.00 | 1.05 | 1.12 | 1.38 |
| 125 μM Red 2 | 1.00 | 1.00 | 1.00 | 1.00 |

TABLE 19

Red Food Dye No. 3 - Average 8 bulls

|  | 30 Min | 45 Min | 60 Min | 75 Min |
|---|---|---|---|---|
| Control - 0 μM Red 3 | 1.07 | 1.23 | 1.58 | 1.80 |
| 15 μM Red 3 | 1.05 | 1.43 | 1.78 | 1.79 |
| 45 μM Red 3 | 1.05 | 1.36 | 1.58 | 1.60 |
| 125 μM Red 3 | 1.00 | 1.02 | 1.10 | 1.32 |

TABLE 20

Phenol Red - Average 8 bulls

|  | 30 Min | 45 Min | 60 Min | 75 Min |
|---|---|---|---|---|
| Control - 0 μM Red 3 | 1.07 | 1.23 | 1.58 | 1.80 |
| 15 μM Red 3 | 1.14 | 1.30 | 1.77 | 1.87 |
| 45 μM Red 3 | 1.01 | 1.36 | 1.68 | 1.81 |
| 125 μM Red 3 | 1.08 | 1.42 | 1.73 | 1.84 |

TABLE 21

Red Food Dye No. 4 - Average 8 bulls

|  | 30 Min | 45 Min | 60 Min | 75 Min |
|---|---|---|---|---|
| Control - 0 µM Red 4 | 1.07 | 1.23 | 1.58 | 1.80 |
| 15 µM Red 4 | 1.09 | 1.44 | 1.79 | 1.91 |
| 45 µM Red 4 | 1.18 | 1.50 | 1.76 | 1.94 |
| 125 µM Red 4 | 1.13 | 1.45 | 1.81 | 1.95 |

As can be easily understood from the foregoing, the basic concepts of the present invention may be embodied in a variety of ways. The invention involves numerous and varied embodiments of staining sperm for sex sorting including, but not limited to, the best mode of the invention.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of "sorter" should be understood to encompass disclosure of the act of "sorting"—whether explicitly discussed or not—and, conversely, were there effectively disclosure of the act of "sorting", such a disclosure should be understood to encompass disclosure of a "sorter" and even a "means for sorting." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

Moreover, for the purposes of the present invention, the term "a" or "an" entity refers to one or more of that entity. As such, the terms "a" or "an", "one or more" and "at least one" can be used interchangeably herein.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

We claim:

1. A sperm suspension comprising: viable, sperm having a DNA selective fluorescent dye associated with nuclear DNA;
   a medium supporting sperm viability;
   a second dye that permeates the membranes of compromised sperm and quenches fluorescence emitted from the DNA selective fluorescent dye, the second dye having a first local absorption maximum wavelength; and
   a third dye that quenches fluorescence noise, the third dye having a second local absorption maximum wavelength that is greater than the first local absorption wavelength of the second dye.

2. The sperm suspension of claim 1 further comprising an intermediate product collected from a flow cytometer.

3. The sperm suspension of claim 1 further comprising an inseminate having trace amounts of the second dye and the third dye.

4. The sperm suspension of claim 1 wherein the sperm suspension is frozen.

5. The sperm suspension of claim 1, wherein the second dye and the third dye are different color dyes.

6. The sperm suspension of claim 1, wherein the third dye is impedance matched to non-specific noise.

7. The sperm suspension of claim 1, wherein the third dye is split enhancing dye.

8. The sperm suspension of claim 1, wherein the third dye absorbs fluorescence emissions having a wavelength within the range of about 520 nm to about 600 nm.

9. The sperm suspension of claim 1, wherein local absorption maximum wavelength of the third dye is about 520 nm.

10. The sperm suspension of claim 1, wherein the viable sperm comprises a gender enriched population of sperm.

11. The sperm suspension of claim 1, wherein the viable sperm comprises a sex sorted population of sperm.

12. The sperm suspension of claim 1, wherein the second dye is a dead quenching dye.

13. The sperm suspension of claim 1, wherein the sperm suspension comprises a flow sorted sperm suspension.

14. The sperm suspension of claim 1, wherein the sperm suspension comprises an artificial inseminate.

\* \* \* \* \*